United States Patent
Lerchen et al.

(10) Patent No.: US 8,334,284 B2
(45) Date of Patent: Dec. 18, 2012

(54) AMINOACYL PRODRUG DERIVATIVES AND MEDICAMENTS FOR THE TREATMENT OF THROMBOEMBOLITIC DISORDERS

(75) Inventors: Hans-Georg Lerchen, Leverkusen (DE); Ursula Krenz, Leichlingen (DE); Karl-Heinz Schlemmer, Wuppertal (DE); Elisabeth Perzborn, Wuppertal (DE); Joerg Keldenich, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/328,532

(22) Filed: Dec. 16, 2011

(65) Prior Publication Data

US 2012/0088761 A1    Apr. 12, 2012

Related U.S. Application Data

(63) Continuation of application No. 12/224,007, filed as application No. PCT/EP2007/001135 on Feb. 6, 2007, now Pat. No. 8,101,601.

(30) Foreign Application Priority Data

Feb. 16, 2006 (DE) .......................... 10 2006 007 146

(51) Int. Cl.
    *A61K 31/5375* (2006.01)
(52) U.S. Cl. ................................... 514/230.8
(58) Field of Classification Search ............... 514/230.8; 544/137
See application file for complete search history.

(56) References Cited

U.S. PATENT DOCUMENTS

| 7,157,456 | B2 | 1/2007 | Straub et al. |
| 7,351,823 | B2 | 4/2008 | Berwe et al. |
| 7,592,339 | B2 | 9/2009 | Straub et al. |
| 7,767,702 | B2 | 8/2010 | Straub et al. |
| 2003/0153610 | A1 | 8/2003 | Straub et al. |
| 2007/0026065 | A1 | 2/2007 | Benke et al. |
| 2008/0026057 | A1 | 1/2008 | Benke |
| 2008/0306070 | A1 | 12/2008 | Perzborn et al. |

FOREIGN PATENT DOCUMENTS

WO    2005060940 A2    7/2005

OTHER PUBLICATIONS

Ansell, et al.:"Managing Oral Anticoagulant Therapy," Chest, 2001, 119:22S-38S.
Casmiro-Garcia, et al.:"Progress in the Discovery of Factor Xa Inhibitors," Expert Opin. Ther. Patents, Feb. 2006, 16(2): 119-145.
Escolar, et al.:"Argatroban: A Direct Thrombin Inhibitor with Reliable and Predictable Anticoagulant Actions," Drugs of Today, 2006, 42(4):223-236.
Hauptman, et al.:"Synthetic Inhibitors of Thrombin and Factor Xa: From Bench to Bedside," Thrombosis Research, 1999, 93: 203-241.
Hirsh, et al.:"Oral Anticoagulants: Mechanism of Action, Clinical Effectiveness, and Optimal Therapeutic Range," Chest, 2001, 119:8S-21S.
Linkins, et al.:"New Anticoagulant Therapy," Annu. Rev. Med., 2005, 56:63-77.
Quan, et al.:"The Race to an Orally Active Factor Xa Inhibitor: Recent Advances," Current Opinion in Drug Discovery & Development, 2004, 7(4): 460-469.
Raghavan, et al.:"Recent Advances in the Status and Targets of Antithrombotic Agents," Drugs of the Future, 2002, 27 (7):669-683.
Reuf, et al.:"New Antithrombotic Drugs on the Horizon," Expert Opin. Investig. Drugs, 2003, 12(5): 781-797.
U.S. Appl. No. 12/438,097, filed Dec. 28, 2009.
U.S. Appl. No. 12/665,718, filed Dec. 20, 2009.
U.S. Appl. No. 12/665,729, filed Dec. 21, 2009.
US Board of Patent Appeals and Interferences opinion in Ex parte Reid W. Von Borstel and Joel A Saydoff, Appeal 2009-006985, U.S. Appl. No. 09/930,494 (Nov. 18, 2009).
US Board of Patent Appeals and Interferences opinion in Ex parte Staley Brod, Appeal 2009-003330, U.S. Appl. No. 10/810,277 (Dec. 29, 2009).
Nigel Mackman, "Triggers, targets, and treatments for thrombosis," Nature vol. 451, Feb. 21, 2008, pp. 914-918.

*Primary Examiner* — Kristin Bianchi
(74) *Attorney, Agent, or Firm* — Karen B. King

(57) ABSTRACT

The present application relates to prodrug derivatives of 5-chloro-N-({(5S)-2-oxo-3-[4-(3-oxomorpholin-4-yl)phenyl]-1,3-oxazolidin-5-yl}methyl)thiophene-2-carboxamide, processes for their preparation, their use for the treatment and/or prophylaxis of diseases, and their use for the manufacture of medicaments for the treatment and/or prophylaxis of diseases, especially of thromboembolic disorders.

15 Claims, No Drawings

AMINOACYL PRODRUG DERIVATIVES AND MEDICAMENTS FOR THE TREATMENT OF THROMBOEMBOLITIC DISORDERS

The present application relates to prodrug derivatives of 5-chloro-N-({(5S)-2-oxo-3-[4-(3-oxomorpholin-4-yl)phenyl]-1,3-oxazolidin-5-yl}methyl)thiophene-2-carboxamide, processes for their preparation, their use for the treatment and/or prophylaxis of diseases, and their use for the manufacture of medicaments for the treatment and/or prophylaxis of diseases, especially of thromboembolic disorders.

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393 (2004)]. In order to achieve an optimal profile of effects it is necessary in this connection for the design of the prodrug residue as well as the desired mechanism of liberation to conform very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985.

5-Chloro-N-({(5S)-2-oxo-3-[4-(3-oxomorpholin-4-yl)phenyl]-1,3-oxazolidin-5-yl}methyl)thiophene-2-carboxamide [BAY 59-7939, compound (A)] is an orally effective, direct inhibitor of the serine protease factor Xa which performs an essential function in regulating the coagulation of blood. The compound is currently undergoing in-depth clinical examination as a possible new active pharmaceutical ingredient for the prevention and therapy of thromboembolic disorders [S. Roehrig et al., *J. Med. Chem.* 48, 5900 (2005)].

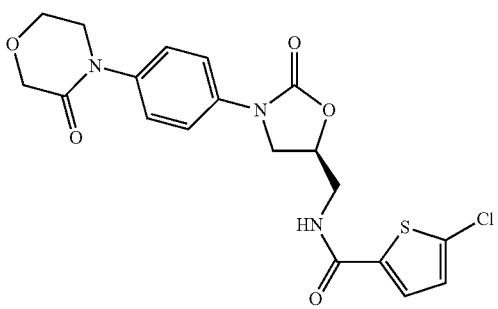

(A)

However, compound (A) has only a limited solubility in water and physiological media, making for example intravenous administration of the active ingredient difficult. It was therefore an object of the present invention to identify derivatives or prodrugs of compound (A) which have an improved solubility in the media mentioned and, at the same time, allow controlled liberation of the active ingredient (A) in the patient's body after administration.

WO 2005/028473 describes acyloxymethylcarbamate prodrugs of oxazolidinones which serve to increase the oral bioavailability. WO 01/00622 discloses acyl prodrugs of carbamate inhibitors of inosine-5'-monophosphate dehydrogenase. A further type of amide prodrugs for oxazolidinones which liberate the underlying active ingredient by a multi-stage activation mechanism is described in WO 03/006440.

The present invention relates to compounds of the general formula (I)

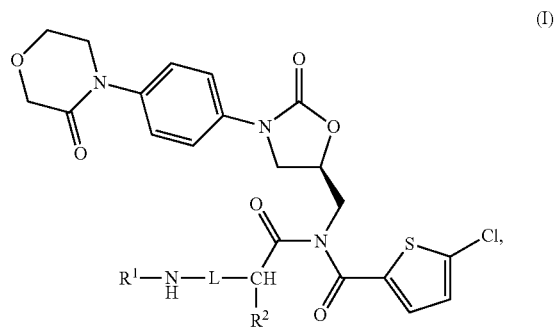

(I)

in which
$R^1$ is hydrogen or $(C_1-C_4)$-alkyl which may be substituted by hydroxy or $(C_1-C_4)$-alkoxy,
$R^2$ is hydrogen or $(C_1-C_4)$-alkyl,
and
L is a $(C_1-C_4)$-alkanediyl group in which one $CH_2$ group may be replaced by an O atom, or is a group of the formula

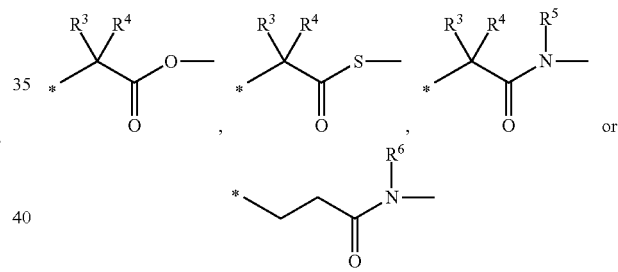

or in which
* means the point of linkage to the N atom,
$R^3$ is the side group of a natural α-amino acid or its homologues or isomers,
or
$R^3$ is linked to $R^1$ and the two together form a $(CH_2)_3$ or $(CH_2)_4$ group,
$R^4$ is hydrogen or methyl,
$R^5$ is $(C_1-C_4)$-alkyl,
and
$R^6$ is hydrogen or $(C_1-C_4)$-alkyl,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

In the context of the present invention, the substituents have the following meaning unless otherwise specified:

$(C_1-C_4)$-Alkyl and $(C_1-C_3)$-alkyl are in the context of the invention a straight-chain or branched alkyl radical having respectively 1 to 4 and 1 to 3 carbon atoms. A straight-chain or branched alkyl radical having 1 to 3 carbon atoms is preferred. Examples which may be preferably mentioned are: methyl, ethyl, n-propyl, isopropyl, n-butyl, iso-butyl, sec-butyl, tert-butyl.

$(C_1-C_4)$-Alkoxy is in the context of the invention a straight-chain or branched alkoxy radical having 1 to 4 carbon atoms. Examples which may be preferably mentioned are: methoxy, ethoxy, n-propoxy, isopropoxy, n-butoxy, tert-butoxy.

$(C_1-C_4)$-Alkanediyl is in the context of the invention a straight-chain or branched divalent alkyl radical having 1 to 4 carbon atoms. A straight-chain alkanediyl radical having 2 to 4 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl.

The side group of an α-amino acid in the meaning of $R^3$ encompasses both the side groups of naturally occurring α-amino acids and the side groups of homologues and isomers of these α-amino acids. The α-amino acid may in this connection have both the L and the D configuration or else be a mixture of the L form and D form. Examples of side groups which may be mentioned are: hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), 3-ureidopropan-1-yl (citrulline). Preferred α-amino acid side groups in the meaning of $R^3$ are hydrogen (glycine), methyl (alanine), propan-2-yl (valine), propan-1-yl (norvaline), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), 3-aminopropan-1-yl (ornithine), 3-guanidinopropan-1-yl (arginine). The L configuration is preferred in each case.

If radicals in the compounds according to the invention are substituted, the radicals may, unless otherwise specified, be substituted one or more times. In the context of the present invention, all radicals which occur more than once have a mutually independent meaning. Substitution by one or two identical or different substituents is preferred. Substitution by one substituent is very particularly preferred.

Preference is given to compounds of the formula (I) in which $R^1$ is hydrogen or $(C_1-C_4)$-alkyl, $R^2$ is hydrogen, and L is a $(C_2-C_4)$-alkanediyl group or is a group of the formula

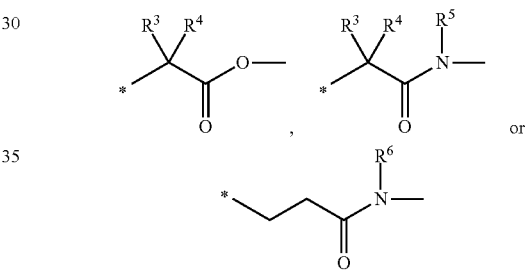

in which

* means the point of linkage to the N atom, $R^3$ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl, or $R^3$ is linked to $R^1$ and the two together form a $(CH_2)_3$ or $(CH_2)_4$ group, $R^4$ is hydrogen or methyl, $R^5$ is methyl, and $R^6$ is hydrogen or methyl, and the salts, solvates and solvates of the salts thereof.

Particularly important in this connection are compounds of the formula (I) in which $R^1$ is hydrogen or $(C_1-C_3)$-alkyl.

Also particularly important are compounds of the formula (I) in which

L is a straight-chain $(C_2-C_4)$-alkanediyl group.

Particular preference is given to compounds of the formula (I) in which $R^1$ is hydrogen, methyl or n-butyl, $R^2$ is hydrogen, and L is a $CH_2CH_2$ group or is a group of the formula

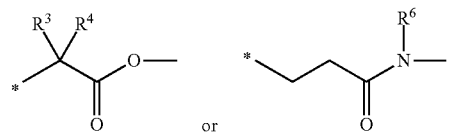

or in which

* means the point of linkage to the N atom, $R^3$ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl, or $R^3$ is linked to $R^1$ and the two together form a $(CH_2)_3$ or $(CH_2)_4$ group, $R^4$ is hydrogen or methyl, and $R^6$ is hydrogen or methyl, and the salts, solvates and solvates of the salts thereof.

Particularly important in this connection are compounds of the formula (I) in which $R^1$ is hydrogen or methyl.

Also particularly important are compounds of the formula (I) in which

L is a $CH_2CH_2$ group.

The invention further relates to a process for preparing the compounds according to the invention of the formula (I), characterized in that either

[A] the compound (A)

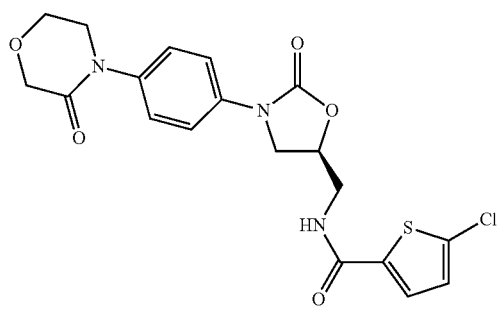

is initially converted in an inert solvent in the presence of a base with a compound of the formula (II)

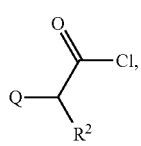

in which $R^2$ has the meaning indicated above, and

Q is a leaving group such as, for example, chlorine, bromine or iodine, into a compound of the formula (III)

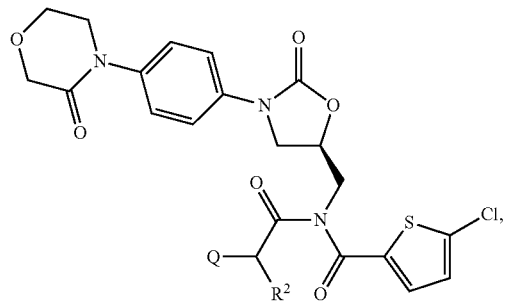

in which Q and $R^2$ have the meanings indicated above, the latter is then reacted in an inert solvent with the caesium salt of an α-amino carboxylic acid or α-amino thiocarboxylic acid of the formula (IV)

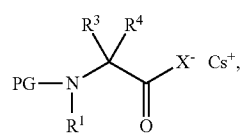

in which $R^1$, $R^3$ and $R^4$ each have the meanings indicated above,

PG is an amino protective group such as, for example, tert-butoxycarbonyl (Boc) or benzyloxycarbonyl (Z), and X is O or S, to give a compound of the formula (V)

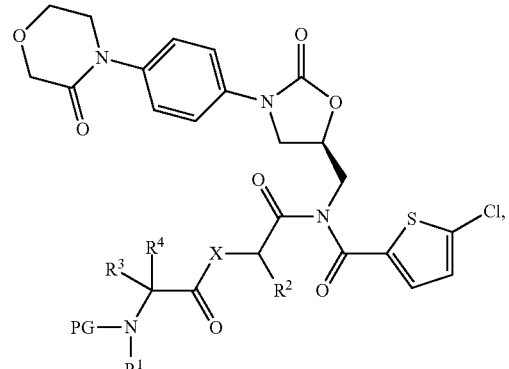

in which $R^1$, $R^2$, $R^3$, $R^4$, PG and X each have the meanings indicated above, and subsequently the protective group PG is removed by conventional methods to result in a compound of the formula (I-A)

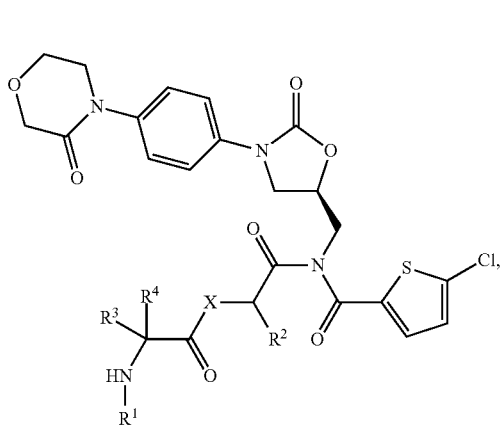
(I-A)

in which $R^1$, $R^2$, $R^3$, $R^4$ and X each have the meanings indicated above, or

[B] compound (A) is reacted in an inert solvent in the presence of a base with a compound of the formula (VI)

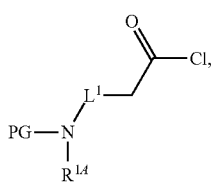
(VI)

in which PG has the meaning indicated above, $R^{1A}$ is ($C_1$-$C_4$)-alkyl which may be substituted by hydroxy or ($C_1$-$C_4$)-alkoxy, and $L^1$ is a ($C_1$-$C_4$)-alkanediyl group in which one $CH_2$ group may be replaced by an O atom, to give a compound of the formula (VII)

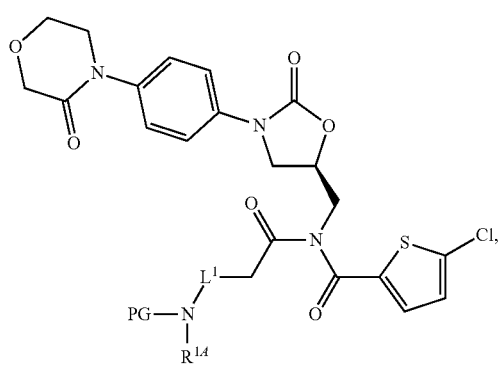
(VII)

in which $R^{1A}$, $L^1$ and PG each have the meanings indicated above, and subsequently the protective group PG is removed by conventional methods to result in a compound of the formula (I-B)

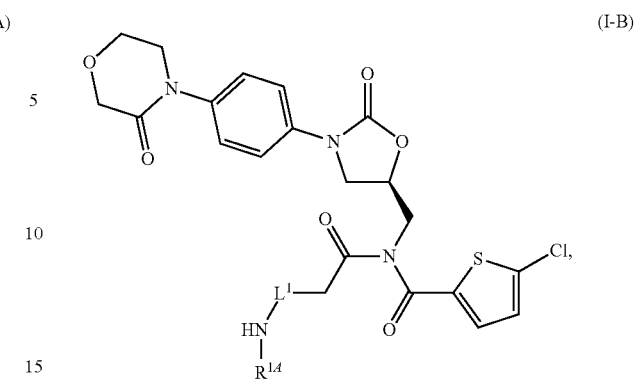
(I-B)

in which $R^{1A}$ and $L^1$ have the meanings indicated above, or

[C] the compound (B)

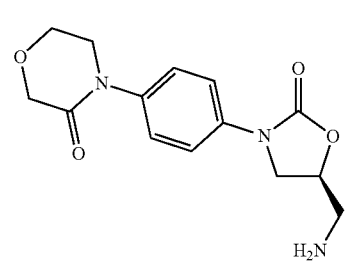
(B)

is initially converted by standard methods of peptide chemistry into a compound of the formula (VIII)

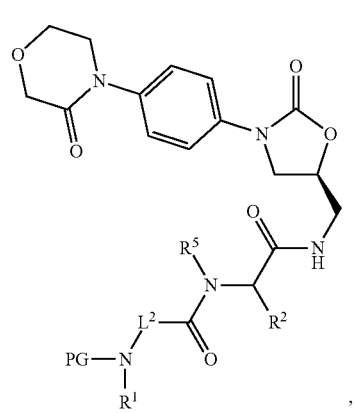
(VIII)

in which PG, $R^1$, $R^2$ and $R^5$ each have the meanings indicated above, and $L^2$ is a $(CH_2)_2$ or $CR^3R^4$ group in which $R^3$ and $R^4$ each have the meanings indicated above, the latter is then reacted in an inert solvent in the presence of a base with a compound of the formula (IX)

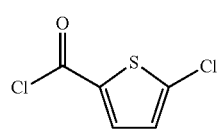
(IX)

S to give a compound of the formula (X)

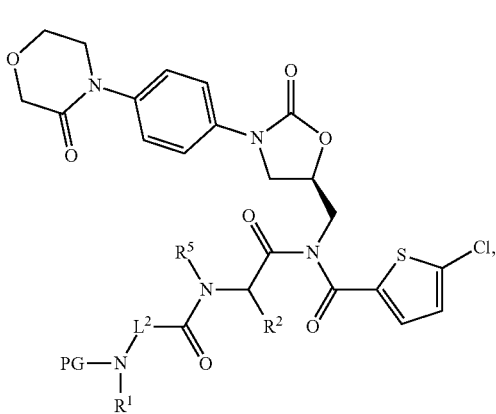

in which PG, $L^2$, $R^1$, $R^2$ and $R^5$ each have the meanings indicated above,
and subsequently the protective group PG is removed by conventional methods to result in a compound of the formula (I-C)

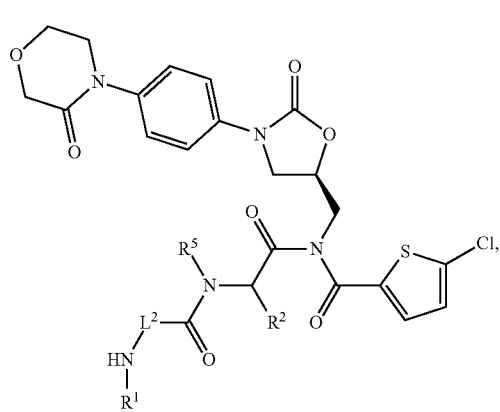

in which $L^2$, $R^1$, $R^2$ and $R^5$ each have the meanings indicated above,
or
[D] compound (A) is reacted in an inert solvent in the presence of a base with a compound of the formula (XI)

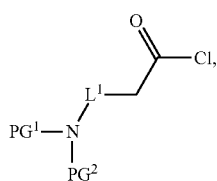

in which
$L^1$ is a $(C_1-C_4)$-alkanediyl group in which one $CH_2$ group may be replaced by an O atom,
and
$PG^1$ and $PG^2$ are independently of one another an amino protective group such as, for example, tert-butoxycarbonyl (Boc), benzyloxycarbonyl (Z) or p-methoxybenzyl (PMB) and may be identical or different, to give a compound of the formula (XII)

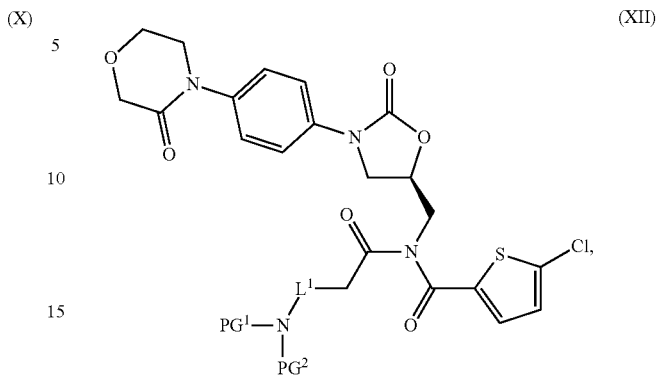

in which $L^1$, $PG^1$ and $PG^2$ each have the meanings indicated above,
and subsequently the protective groups $PG^1$ and $PG^2$ are removed by conventional methods, simultaneously or sequentially, to result in a compound of the formula (I-D)

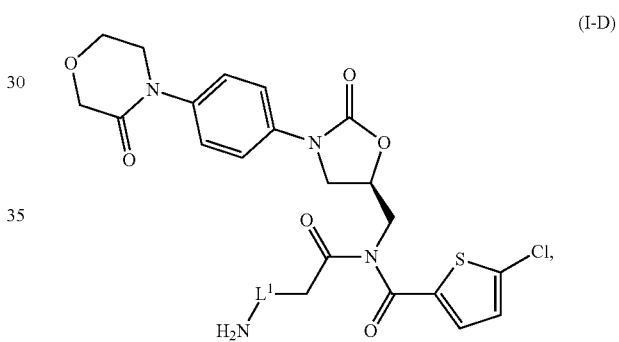

in which $L^1$ has the meaning indicated above,
and the compounds of the formula (I-A), (I-B), (I-C) and (I-D) resulting in each case are converted where appropriate with the appropriate (i) solvents and/or (ii) acids into the solvates, salts and/or solvates of the salts thereof.

The compounds of the formulae (I-A), (I-B), (I-C) and (I-D) may also result directly in the form of their salts in the preparation by the processes described above. These salts can be converted where appropriate by treatment with a base in an inert solvent, by chromatographic methods or by ion exchange resins, into the respective free bases.

Functional groups present where appropriate in the radicals $R^1$, $R^{1A}$ and/or $R^3$ may, if expedient or necessary, also be in temporarily protected form in the reaction sequences described above. The introduction and removal of such protective groups, as well as of the protective groups PG, $PG^1$ and $PG^2$, takes place in this connection by conventional methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984].

Such protective groups which are present where appropriate in $R^1$, $R^{1A}$ and/or $R^3$ may in this connection be removed at the same time as the elimination of PG or in a separate reaction step before or after the elimination of PG.

The amino protective group PG, PG$^1$ or PG$^2$ preferably used in the above processes is tert-butoxycarbonyl (Boc), benzyloxycarbonyl (Z) or p-methoxybenzyl (PMB). Elimination of these protective groups is carried out by conventional methods, preferably by reacting with a strong acid such as hydrogen chloride, hydrogen bromide or trifluoroacetic acid in an inert solvent such as dioxane, dichloromethane or acetic acid; it is also possible where appropriate for the elimination to be carried out without an additional inert solvent.

The transformation (B)→(VIII) takes place by standard methods of peptide chemistry either by acylating the compound (B) with a suitably protected dipeptide derivative or by sequential coupling of the individual amino acid components, suitably protected where appropriate [cf., for example, M. Bodanszky, *Principles of Peptide Synthesis*, Springer-Verlag, Berlin, 1993; H.-D. Jakubke and H. Jeschkeit, *Aminosäuren, Peptide, Proteine*, Verlag Chemie, Weinheim, 1982].

The inert solvents preferably used in process steps (A)+(II)→(III), (A)+(VI)→(VII), (VIII)+(IX)→(X) and (A)+(XI)→(XII) are tetrahydrofuran, N,N-dimethylformamide or dimethyl sulphoxide; N,N-dimethylformamide is particularly preferred. A particularly suitable base in these reactions is sodium hydride. The reactions mentioned are generally carried out in a temperature range from 0° C. to +40° C. under atmospheric pressure.

Process step (III)+(IV)→(V) preferably takes place in N,N-dimethylformamide as solvent. The reaction is generally carried out in a temperature range from 0° C. to +50° C., preferably at +20° C. to +50° C., under atmospheric pressure. The reaction can also be carried out advantageously with ultrasound treatment.

The compounds of the formulae (II), (IV), (VI), (IX) and (XI) are commercially available, known from the literature or can be prepared by processes customary in the literature. Preparation of compounds (A) and (B) is described in S. Roehrig et al., *J. Med. Chem.* 48, 5900 (2005).

Preparation of the compounds according to the invention can be illustrated by the following synthesis schemes:

Scheme 1

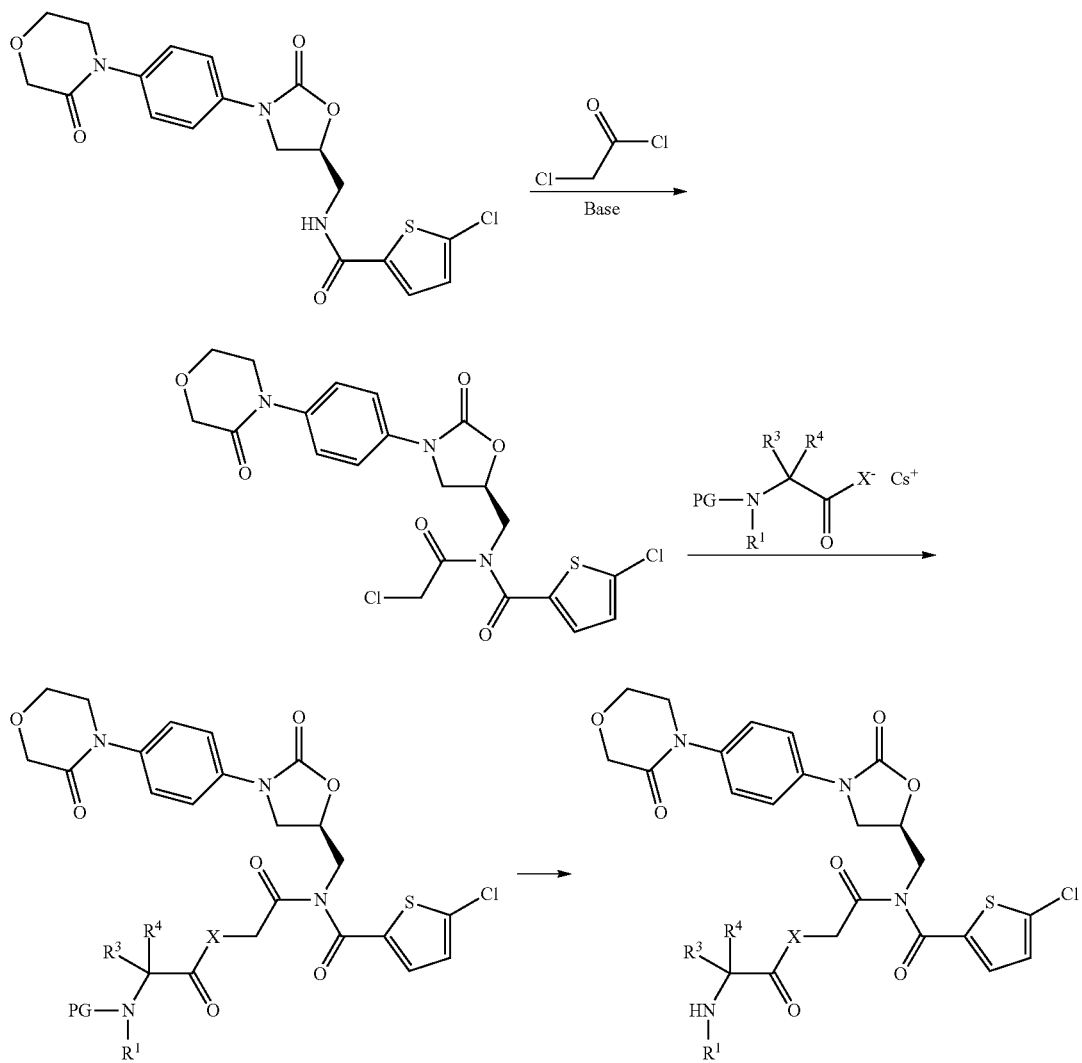

[X = O or S; PG = amino protective group, e.g. tert-butoxycarbonyl (Boc) or benzyloxycarbonyl (Z)].

Scheme 2
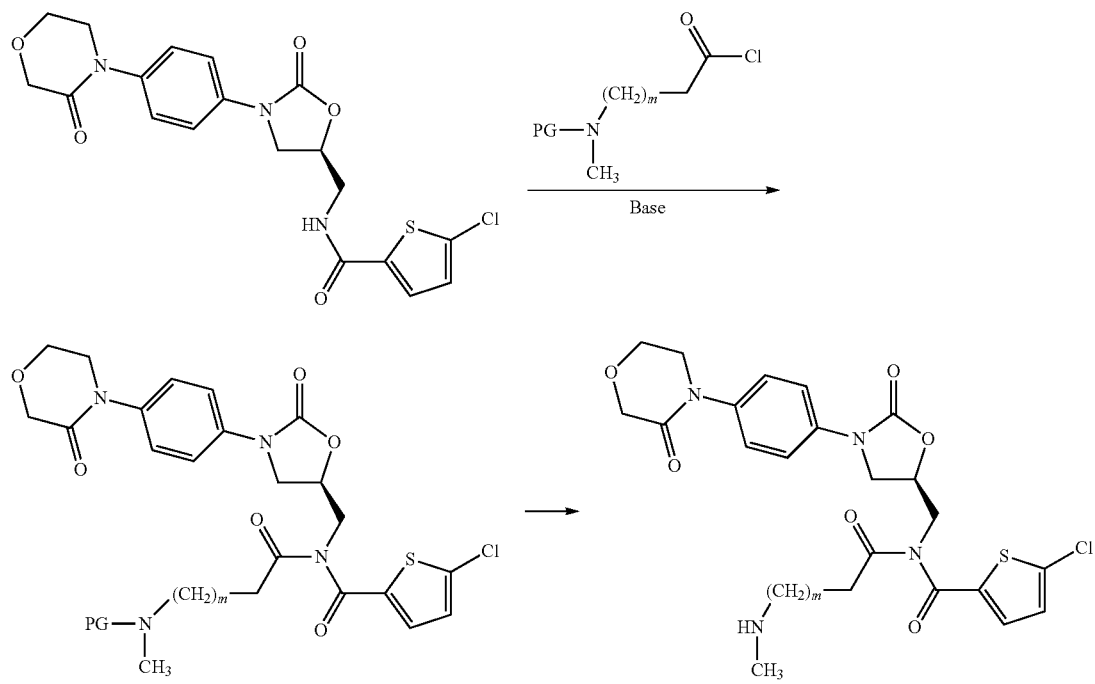
[m = 1-4; PG = amino protective group, e.g. tert-butoxycarbonyl (Boc) or benzyloxycarbonyl (Z)].
Scheme 3
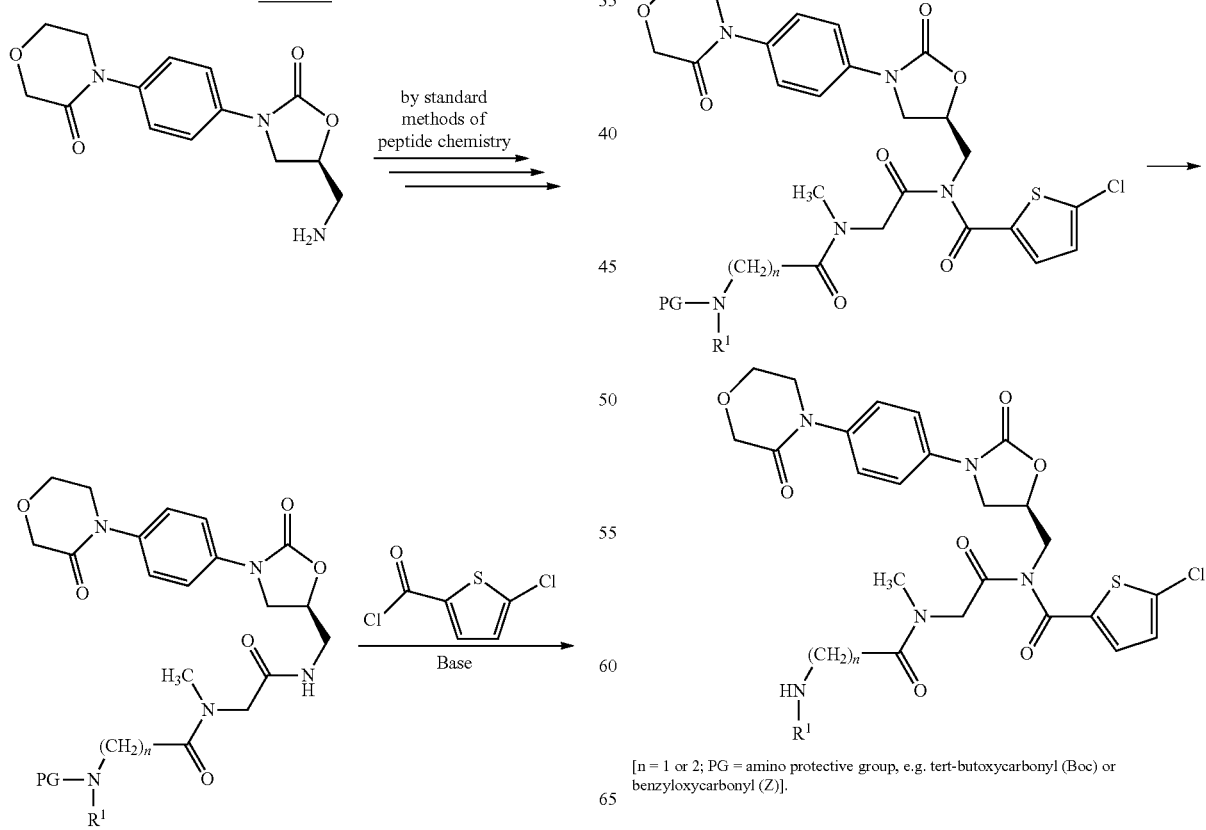
[n = 1 or 2; PG = amino protective group, e.g. tert-butoxycarbonyl (Boc) or benzyloxycarbonyl (Z)].

Scheme 4

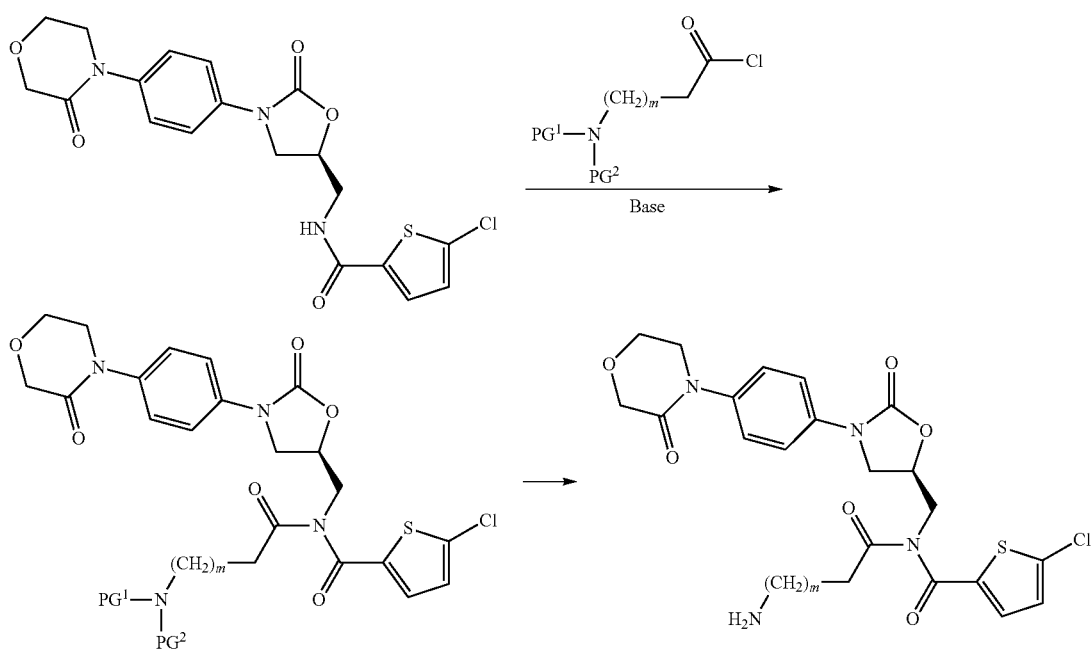

[m = 1-4; PG$^1$, PG$^2$ = amino protective groups, e.g. tert-butoxycarbonyl (Boc) or benzyloxycarbonyl (Z) or p-methoxybenzyl (PMB)].

The compounds according to the invention and their salts represent useful prodrugs of the active ingredient compound (A). On the one hand, they show good stability at pH 4 and, on the other hand, they show efficient conversion into the active ingredient compound (A) at a physiological pH and in vivo. The compounds according to the invention moreover have good solubility in water and other physiologically tolerated media, making them suitable for therapeutic use especially on intravenous administration.

The present invention further relates to the use of the compounds according to the invention for the treatment and/or prophylaxis of disorders, preferably of thromboembolic disorders and/or thromboembolic complications.

The "thromboembolic disorders" include in the context of the present invention in particular disorders such as myocardial infarction with ST segment elevation (STEMI) and without ST segment elevation (non-STEMI), stable angina pectoris, unstable angina pectoris, reocclusions and restenoses following coronary interventions such as angioplasty or aortocoronary bypass, peripheral arterial occlusive diseases, pulmonary embolisms, deep venous thromboses and renal vein thromboses, transient ischaemic attacks, and thrombotic and thromboembolic stroke.

The substances are therefore also suitable for the prevention and treatment of cardiogenic thromboembolisms, such as, for example, cerebral ischaemias, stroke and systemic thromoboembolism and ischaemias, in patients with acute, intermittent or persistent cardiac arrhythmias such as, for example, atrial fibrillation, and those undergoing cardioversion, also in patients with heart valve diseases or with artificial heart valves. The compounds according to the invention are additionally suitable for the treatment of disseminated intravascular coagulation (DIC).

Thromboembolic complications also occur in association with microangiopathic haemolytic anaemia, extracorporeal circulations, such as haemodialysis, and heart valve prostheses.

The compounds according to the invention are additionally suitable also for the prophylaxis and/or treatment of atherosclerotic vascular disorders and inflammatory disorders such as rheumatic disorders of the musculoskeletal system, furthermore likewise for the prophylaxis and/or treatment of Alzheimer's disease. The compounds according to the invention can additionally be employed for inhibiting tumour growth and metastasis formation, for microangiopathies, age-related macular degeneration, diabetic retinopathy, diabetic nephropathy and other microvascular disorders, and for the prevention and treatment of thromoembolic complications such as, for example, venous thromboembolisms in tumour patients, especially those undergoing major surgical procedures or chemotherapy or radiotheraphy.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, especially of the aforementioned disorders, using the compounds according to the invention.

The present invention further relates to medicaments comprising a compound according to the invention and one or more further active ingredients, especially for the treatment and/or prophylaxis of the aforementioned disorders.

Examples of suitable combination active ingredients which may preferably be mentioned are:
lipid-lowering agents, especially HMG-CoA (3-hydroxy-3-methylglutarylcoenzyme A) reductase inhibitors;
coronary therapeutics/vasodilatators, especially ACE (angiotensin converting enzyme) inhibitors, AII (angiotensin II) receptor antagonists; β-adrenoceptor antagonists; alpha-1 adrenoceptor antagonists; diuretics; calcium channel blockers; substances which bring about an increase in cyclic guanosine monophosphate (cGMP), such as, for example, stimulators of soluble guanylate cyclase;

plasminogen activators (thrombolytics/fibrinolytics) and compounds which increase thrombolysis/fibrinolysis, such as inhibitors of plasminogen activator inhibitor (PAI inhibitors) or inhibitors of the thrombin-activated fibrinolysis inhibitor (TAFI inhibitors);

substances having anticoagulant activity (anticoagulants);

platelet aggregation-inhibiting substances (platelet aggregation inhibitors);

fibrinogen receptor antagonists (glycoprotein IIb/IIIa antagonists);

and antiarrhythmics.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary or nasal route. The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation, such as power inhalers or nebulizers, or pharmaceutical forms which can be administered nasally, such as drops, solutions or sprays.

Parenteral administration is preferred, especially intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavours and/or odours.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms abs. absolute
Boc tert-butoxycarbonyl
DMF N,N-dimethylformamide
DMSO dimethyl sulphoxide
h hour(s)
HPLC high pressure, high performance liquid chromatography
LC-MS coupled liquid chromatography-mass spectrometry
min minute(s)
MS mass spectrometry
NMR nuclear magnetic resonance spectrometry
p para
Pd/C palladium on activated carbon
PMB p-methoxybenzyl
quant. quantitative (for yield)
$R_f$ retention index (for TLC)
RT room temperature
$R_t$ retention time (for HPLC)
TLC thin-layer chromatography
UV ultraviolet spectrometry
v/v volume to volume ratio (of a solution)
Z benzyloxycarbonyl
LC-MS and HPLC Methods:
Method 1 (Preparative HPLC):
 Column: VP 250/21 Nukleodur 100-5 C18 ec, Macherey & Nagel No. 762002; eluent A: water/0.01% trifluoroacetic acid, eluent B: acetonitrile/0.01% trifluoroacetic acid; gradient: 0 min 0% B→20 min 20% B→40 min 20% B→60 min 30% B→80 min 30% B→90 min 100% B→132 min 100% B; flow rate: 5 ml/min; temperature: RT; UV detection: 210 nm.
Method 2 (Analytical HPLC):
 Column: XTerra 3.9×150 WAT 186000478; eluent A: 10 ml of 70% perchloric acid in 2.5 litres of water, eluent B: acetonitrile; gradient 0.0 min 20% B→1 min 20% B→4 min 90% B→9 min 90% B; temperature: RT; flow rate: 1 ml/min.
Method 3 (LC-MS):
Instrument: Micromass LCT with HPLC Agilent Series 1100; column: Waters Symmetry C18, 3.5 µm, 50 mm×2.1 mm; eluent A: 1 l of water+1 ml of 98-100% formic acid, eluent B: 1 l of acetonitrile+1 ml of 98-100% formic acid; gradient: 0 min 100% A→1 min 100% A→6 min 10% A→8 min 0% A→10 min 0% A→10.1 min 100% A→12 min 100% A; flow rate: 0-10 min 0.5 ml/min→10.1 min 1 ml/min→12 min 0.5 ml/min; temperature: 40° C.; UV detection DAD: 208-500 nm.
Method 4 (LC-MS):
Instrument: Micromass ZQ with HPLC HP 1100 Series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 210 nm.
Method 5 (LC-MS):
Instrument: Micromass Quattro LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 208-400 nm.
Method 6 (LC-MS):
MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 210 nm.
Method 7 (Chiral HPLC, Analytical):
Chiral silica gel phase (250 mm×4.6 mm) based on poly (N-methacryloyl-L-leucine dicyclopropylmethylamide); eluent: isohexane/ethyl acetate 35:65 (v/v); temperature: 24° C.; flow rate: 2 ml/min; UV detection: 270 nm.
Method 8 (Chiral HPLC, Analytical):
Chiral silica gel phase (250 mm×4.6 mm) based on poly (N-methacryloyl-L-leucine tert-butylamide); eluent: isohexane/ethyl acetate 35:65 (v/v); temperature: 24° C.; flow rate: 2 ml/min; UV detection: 270 nm.
Method 9 (Chiral HPLC, Analytical):
Chiral silica gel phase (250 mm×4.6 mm) based on poly (N-methacryloyl-L-leucine tert-butylamide); eluent: isohexane/ethyl acetate 65:35 (v/v); temperature: 24° C.; flow rate: 2 ml/min; UV detection: 270 nm.
Method 10 (Chiral HPLC, Preparative):
Chiral silica gel phase (670 mm×40 mm) based on poly(N-methacryloyl-L-leucine dicyclopropylmethylamide); eluent: isohexane/ethyl acetate 25:75 (v/v); temperature: 24° C.; flow rate: 80 ml/min; UV detection: 270 nm.
Method 11 (Chiral HPLC, Preparative):
Chiral silica gel phase (670 mm×40 mm) based on poly(N-methacryloyl-L-leucine tert-butylamide); eluent: isohexane/ethyl acetate 65:35 (v/v); temperature: 24° C.; flow rate: 50 ml/min; UV detection: 260 nm.
Method 12 (LC-MS):
Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.
Method 13 (LC-MS):
Instrument: Micromass Platform LCZ with HPLC Agilent Series 1100; column: Thermo Hypersil GOLD 3µ, 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.
NMR Spectrometry:
NMR measurements were carried out at a proton frequency of 400.13 MHz. The samples were normally dissolved in DMSO-$d_6$; temperature: 302 K.
Starting Compounds and Intermediates:
The starting materials used were 5-chloro-N-({(5S)-2-oxo-3-[4-(3-oxomorpholin-4-yl)phenyl]-1,3-oxazolidin-5-yl}methyl)thiophene-2-carboxamide [compound (A)] and 4-{4-[(5S)-5-(aminomethyl)-2-oxo-1,3-oxazolidin-3-yl]phenyl}morpholin-3-one [compound (B)], preparation of which is described elsewhere [S. Roehrig et al., *J. Med. Chem.* 48, 5900 (2005)].

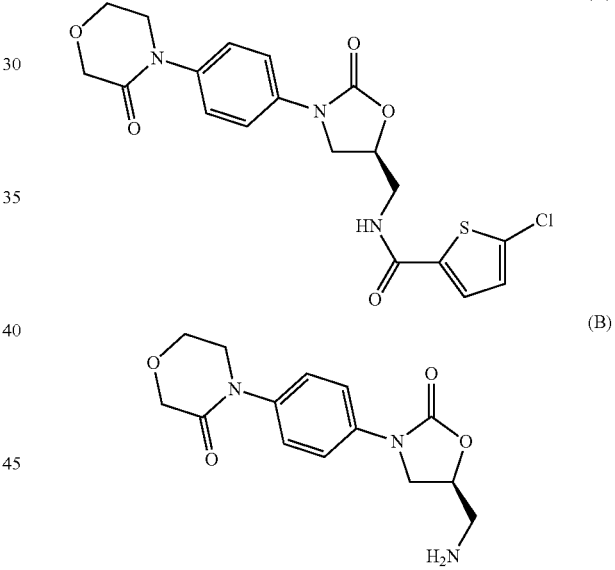

General Procedure 1 for Acylating the Amino Group in Compound (B):
The carboxyl components employed (in most cases suitably protected amino acid or peptide derivatives) are either commercially available or are prepared by standard methods. 4-{4-[(5S)-5-(Aminomethyl)-2-oxo-1,3-oxazolidin-3-yl]phenyl}morpholin-3-one [compound (B)] is preferably acylated directly with suitably protected peptide derivatives. In an alternative sequential procedure it is also possible firstly to link to an amino acid derivative, subsequently deprotect where appropriate and then react with further suitably protected amino acid or peptide derivatives by standard methods.
2.3 mmol of the appropriate carboxyl component are dissolved in 30 ml of DMF, and 2.3 mmol of 1-hydroxy-1H-benzotriazole, 2 mmol of N-(3-dimethylaminopropyl)-N'-ethylcarbodiimide hydrochloride (EDC), 4.5 mmol of N,N-diisopropylethylamine and then 1.5 mmol of the amine component, 4-{4-[(5S)-5-(aminomethyl)-2-oxo-1,3-oxazolidin-3-yl]phenyl}morpholin-3-one [compound (B)] are added. The reaction mixture is stirred at room temperature for 3 h and then concentrated, and the residue is taken up in dichloromethane and extracted twice with 5% strength citric acid, twice with 5% strength sodium bicarbonate solution and twice with water. The organic phase is concentrated and the residue is purified by flash chromatography on silica gel with acetonitrile/water 30:1 as eluent. The appropriate fractions are combined and the solvent is removed. The remaining residue is dissolved in dichloromethane/methanol, and the product is precipitated with diethyl ether and dried under high vacuum.

Intermediate 1A

5-Chloro-N-(chloroacetyl)-N-({(5S)-2-oxo-3-[4-(3-oxomorpholin-4-yl)phenyl]-1,3-oxazolidin-5-yl}methyl)thiophene-2-carboxamide

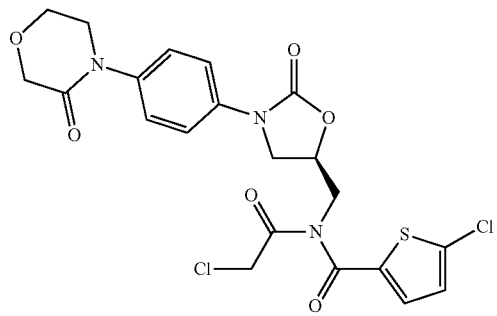

1 g (2.3 mmol) of 5-chloro-N-({(5S)-2-oxo-3-[4-(3-oxomorpholin-4-yl)phenyl]-1,3-oxazolidin-5-yl}methyl)thiophene-2-carboxamide [compound (A)] is dissolved in 170 ml of abs. DMF under argon. 110 mg (4.6 mmol) of sodium hydride are added, and the mixture is stirred at RT for 20 min. Then 3.5 g (31 mmol) of chloroacetyl chloride are added, keeping the reaction temperature at RT. After 30 min, 25 ml of water are added while cooling, and the mixture is left to stand at RT for two days. The solvent is then removed in vacuo, during which the temperature should not rise above +25° C. The residue is taken up in 500 ml of dichloromethane and extracted five times with 200 ml of water. The organic phase is dried over magnesium sulphate, filtered and concentrated to a volume of about 50 ml. While stirring, 200 ml of diethyl ether are added, and the precipitate (mostly unreacted starting material) is then filtered off. The mother liquor is concentrated and the residue is purified by flash chromatography on silica gel with toluene/ethanol 10:1 as eluent. The appropriate fractions are combined, and the solvent is removed. The residue is lyophilized from dioxane.

Yield: 111 mg (9.5% of theory)

HPLC (method 2): $R_t$=5.09 min;

LC-MS (method 4): $R_t$=2.31 min; m/z=512 (M+H)$^+$.

Intermediate 2A

N-[(Benzyloxy)carbonyl]-N-methylglycyl-N$^2$-methyl-N-({(5S)-2-oxo-3-[4-(3-oxomorpholin-4-yl)phenyl]-1,3-oxazolidin-5-yl}methyl)glycinamide

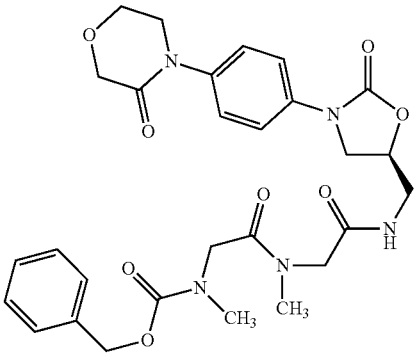

In the first step, 511 mg (1.5 mmol) of Z-sarcosine are reacted as carboxyl component by General Procedure 1 with compound (B) (yield: 697 mg, 92% of theory).

The benzyloxycarbonyl protective group is then removed from 200 mg (0.4 mmol) of this intermediate by hydrogenolysis over Pd/C by standard methods (yield: 130 mg, 89% of theory).

The compound obtained in this way is then linked in a third step again to 120 mg (0.54 mmol) of Z-sarcosine by General Procedure 1 (yield: 201 mg, 98% of theory).

HPLC (method 2): $R_t$=4.21 min;

LC-MS (method 6): $R_t$=1.54 min; m/z=568 (M+H)$^+$.

Intermediate 3A

N-[(Benzyloxy)carbonyl]-N-methylglycyl-N$^2$-methyl-N-({(5S)-2-oxo-3-[4-(3-oxomorpholin-4-yl)phenyl]-1,3-oxazolidin-5-yl}methyl)-L-valinamide

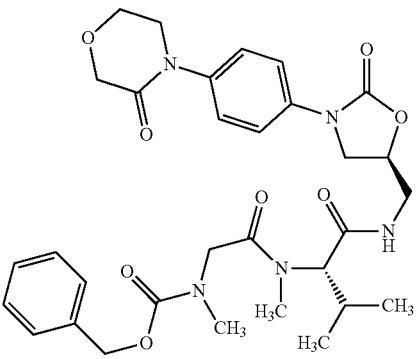

In the first step, 529 mg (2.3 mmol) of Boc-N-methylvaline are reacted as carboxyl component by General Procedure 1 with compound (B) (yield: 750 mg, 97% of theory).

The tert-butoxycarbonyl protective group is then removed from 750 mg (1.5 mmol) of this intermediate with trifluoroacetic acid in dichloromethane by a standard method (yield: 740 mg, 96% of theory).

200 mg (0.39 mmol) of the compound obtained in this way are then linked in a third step to 129 mg (0.58 mmol) of Z-sarcosine by General Procedure 1 (yield: 206 mg, 88% of theory).

HPLC (method 2): $R_t$=4.68 min;
LC-MS (method 5): $R_t$=1.96 min; m/z=610 (M+H)$^+$.

Intermediate 4A

Benzyl methyl-{5-oxo-5-[({(5S)-2-oxo-3-[4-(3-oxo-morpholin-4-yl)phenyl]-1,3-oxazolidin-5-yl}-methyl)amino]pentyl}carbamate

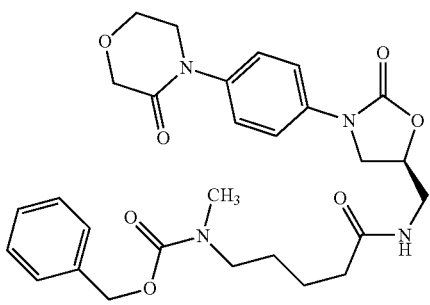

32 mg (0.119 mmol) of 5-[[(benzyloxy)carbonyl](methyl)amino]valeric acid are reacted as carboxyl component by General Procedure 1 with compound (B).

Yield: 45 mg (91% of theory)
HPLC (method 2): $R_t$=4.51 min;
LC-MS (method 4): $R_t$=2.02 min; m/z=539 (M+H)$^+$.

Intermediate 5A

Benzyl methyl{5-oxo-5-[({(5S)-2-oxo-3-[4-(3-oxo-morpholin-4-yl)phenyl]-1,3-oxazolidin-5-yl}-methyl)amino]butyl}carbamate

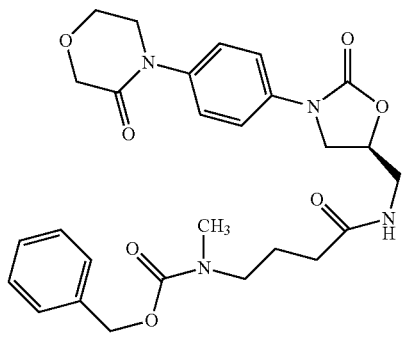

313 mg (0.96 mmol) of 5-[[(benzyloxy)carbonyl](methyl)amino]butyric acid are reacted as carboxyl component by General Procedure 1 with compound (B).

Yield: 298 mg (71% of theory)
HPLC (method 2): $R_t$=4.42 min;
LC-MS (method 4): $R_t$=1.89 min; m/z=525 (M+H)$^+$.

Intermediate 6A

N-[(Benzyloxy)carbonyl]-N-methyl-β-alanyl-N$^2$-methyl-N-({(5S)-2-oxo-3-[4-(3-oxomorpholin-4-yl)phenyl]-1,3-oxazolidin-5-yl}methyl)glycinamide

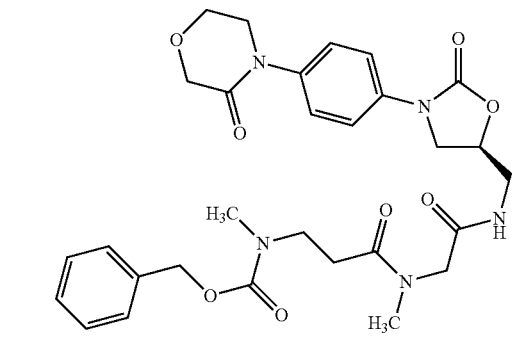

In the first step, 511 mg (1.5 mmol) of Z-sarcosine are reacted as carboxyl component by General Procedure 1 with compound (B) (yield: 697 mg, 92% of theory).

The benzyloxycarbonyl protective group is then removed from 200 mg (0.4 mmol) of this intermediate by hydrogenolysis over Pd/C by standard methods (yield: 130 mg, 89% of theory).

100 mg of the compound obtained in this way are then linked in a third step to 98.2 mg (0.41 mmol) of Z-N-methyl-β-alanine by General Procedure 1 (yield: 87 mg, 54% of theory).

HPLC (method 2): $R_t$=4.28 min;
LC-MS (method 6): $R_t$=1.60 min; m/z=582 (M+H)$^+$.

Intermediate 7A

Benzyl(4-chloro-4-oxobutyl)methylcarbamate

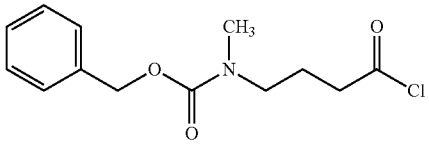

Firstly, 4-[[(benzyloxy)carbonyl](methyl)amino]butyric acid is prepared by a literature procedure [Y. Aramaki et al., *Chem. Pharm. Bull.* 52, 258 (2004)] from commercially available 4-{[(benzyloxy)carbonyl]amino}butyric acid. An alternative preparation is also to introduce the benzyloxycarbonyl protective group into ω-N-methylaminoalkylcarboxylic acids which are obtainable according to P. Quitt et al. [*Helv. Chim. Acta* 46, 327 (1963)].

1.74 g (6.92 mmol) of 4-[[(benzyloxy)carbonyl](methyl)amino]butyric acid are dissolved in 35 ml of dichloromethane and 3.5 ml (48 mmol) of thionyl chloride are added. The mixture is heated under reflux for 1 h. It is then concentrated in vacuo, and the residue is again mixed with dichloromethane and concentrated once again. A viscous oil remains and is dried under high vacuum. 1.8 g (96% of theory) of the target compound are obtained and are reacted further without further purification and characterization.

Intermediate 8A

Benzyl(5-chloro-5-oxopentyl)methylcarbamate

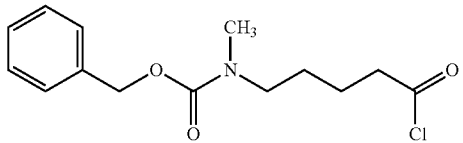

Firstly, 5-[[(benzyloxy)carbonyl](methyl)amino]valeric acid is prepared by known methods in analogy to Intermediate 7A.

1.97 g (7.43 mmol) of 5-[[(benzyloxy)carbonyl](methyl)amino]valeric acid are dissolved in 30 ml of dichloromethane, and 4.9 ml (67.3 mmol) of thionyl chloride are added. The mixture is heated under reflux for 1 h. It is then concentrated in vacuo, and the residue is again mixed with dichloromethane and concentrated once again. A viscous oil remains and is dried under high vacuum. 2 g (95% of theory) of the target compound are obtained and are reacted further without further purification and characterization.

Intermediate 9A

Benzyl(3-chloro-3-oxopropyl)methylcarbamate

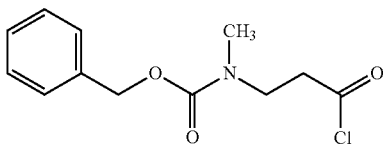

Firstly, 3-[[(benzyloxy)carbonyl](methyl)amino]propionic acid is prepared by a literature procedure [Y. Aramaki et al., Chem. Pharm. Bull. 52, 258 (2004)] from commercially available 3-{[(benzyloxy)carbonyl]amino}propionic acid. An alternative preparation is also to introduce the benzyloxycarbonyl protective group into ω-N-methylaminoalkylcarboxylic acids which are obtainable according to P. Quitt et al. [Helv. Chim. Acta 46, 327 (1963)].

850 mg (3.58 mmol) of 3-[[(benzyloxy)carbonyl](methyl)amino]propionic acid are dissolved in 15 ml of dichloromethane, and 1.5 ml of oxalyl chloride are added. The mixture is heated under reflux for 3 h. It is then concentrated in vacuo, and the residue is again mixed with dichloromethane and concentrated once again. A viscous oil remains and is dried under high vacuum. 915 mg (quant.) of the target compound are obtained and are reacted further without further purification and characterization.

Intermediate 10A

Benzyl(6-chloro-6-oxohexyl)methylcarbamate

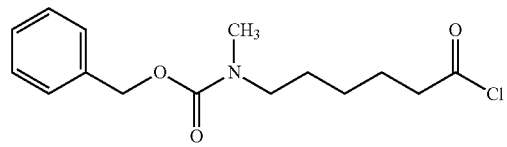

Firstly, 6-[[(benzyloxy)carbonyl](methyl)amino]caproic acid is prepared by a literature procedure [Y. Aramaki et al., Chem. Pharm. Bull. 52, 258 (2004)] from commercially available 6-{[(benzyloxy)carbonyl]amino}caproic acid. An alternative preparation is also to introduce the benzyloxycarbonyl protective group into ω-N-methylaminoalkylcarboxylic acids which are obtainable according to P. Quitt et al. [Helv. Chim. Acta 46, 327 (1963)].

3850 mg (13.8 mmol) of 6-[[(benzyloxy)carbonyl](methyl)amino]caproic acid are dissolved in 60 ml of dichloromethane, and 4 ml of oxalyl chloride are added. The mixture is heated under reflux for 3 h. It is then concentrated in vacuo, and the residue is again mixed with dichloromethane and concentrated once again. A viscous oil remains and is dried under high vacuum. 4.1 g (quant.) of the target compound are obtained and are reacted further without further purification and characterization.

Intermediate 11A

5-Chlorothiophene-2-carbonyl chloride

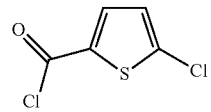

480 mg (2.95 mmol) of 5-chlorothiophene-2-carboxylic acid are dissolved in 24 ml of dichloromethane, and 2.4 ml (27.5 mmol) of oxalyl chloride are added. The mixture is heated under reflux for 16 h. It is then concentrated in vacuo, and the residue is again mixed with dichloromethane and concentrated once again. A viscous oil remains and is dried under high vacuum. 534 mg (quant.) of the target compound are obtained and are reacted further without further purification and characterization.

Intermediate 12A

Benzyl(5-chloro-5-oxopentyl)(4-methoxybenzyl)carbamate

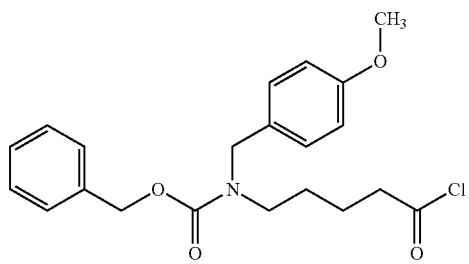

Stage a):

10 g (85.4 mmol) of 5-aminovaleric acid, 17.4 g (128 mmol) of p-anisaldehyde and 10.3 g (85.4 mmol) of magnesium sulphate are taken up in 330 ml of ethanol and heated under reflux for 1 h. The solid is then filtered off and washed with ethanol, and subsequently a total of 1.94 g (51.2 mmol) of sodium borohydride are added in portions to the filtrate over the course of 15 min. Firstly 10 ml of water are added, and then 128 ml of a 2 M sodium hydroxide solution. After 5 min, the mixture is diluted with 300 ml of water and then extracted three times with 200 ml of ethyl acetate each time. The aqueous phase is adjusted to pH 2 with 4 M hydrochloric acid and concentrated in vacuo. The residue is purified by flash chromatography on silica gel with acetonitrile/water/acetic acid 5:1:0.1 as eluent. The product fractions are concentrated and stirred with ethyl acetate and diethyl ether. The residue is then filtered off with suction and dried under high vacuum. 9.1 g (45% of theory) of the p-methoxybenzyl-protected 5-aminovaleric acid are obtained.

Stage b):

The 5-aminovaleric acid derivative obtained in this way is taken up in dioxane/water (1:1) and adjusted to pH 10 with sodium hydroxide solution, and then 12.97 g (76 mmol) of benzyl chlorocarbonate are added dropwise. After stirring at RT for 15 min, the dioxane is removed in vacuo and the remaining solution is adjusted to pH 2 with 2 M hydrochloric acid. The organic phase after extraction with ethyl acetate is washed twice with water. The organic phase is then concentrated and the residue is dried under high vacuum. This is followed by purification by flash chromatography on silica gel with acetonitrile as eluent. The product fractions are concentrated and the residue is dried under high vacuum. 5.6 g (38% of theory) of the Z-protected amino acid are obtained.

LC-MS (method 3): $R_t$=2.47 min; m/z=372 (M+H)$^+$.

Stage c):

5.6 g (15 mmol) of the 5-{[(benzyloxy)carbonyl](4-methoxybenzyl)amino}valeric acid obtained in this way are dissolved in 60 ml of dichloromethane, and 2.2 ml of thionyl chloride are added. The mixture is heated under reflux for 30 min. It is then concentrated in vacuo, and the residue is again mixed with dichloromethane and concentrated once again. A viscous oil remains and is dried under high vacuum. 5.7 g (98% of theory) of the target compound are obtained and are reacted further without further purification and characterization.

Intermediate 13A

Benzyl(6-chloro-6-oxohexyl)(4-methoxybenzyl)carbamate

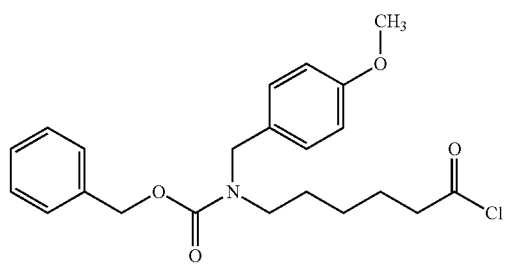

The title compound is prepared in analogy to Intermediate 12A starting from 6-aminocaproic acid.

Intermediate 14A

Benzyl(4-chloro-4-oxobutyl)(4-methoxybenzyl)carbamate

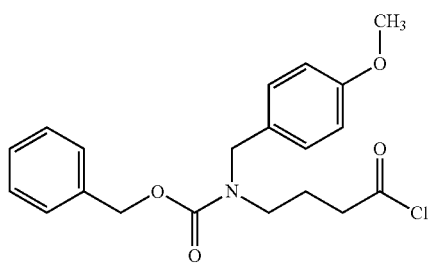

The title compound is prepared in analogy to Intermediate 12A starting from 4-aminobutyric acid.

Intermediate 15A

Benzyl butyl(4-chloro-4-oxobutyl)carbamate

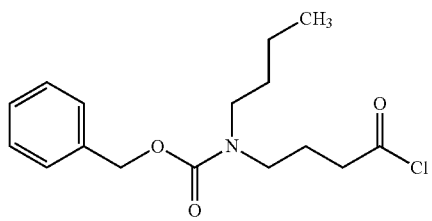

Firstly, 4-{[(benzyloxy)carbonyl](butyl)amino}butyric acid is prepared by a literature procedure [*Org. Prep. Proc. Int.* 9 (2), 49 (1977)] in conjunction with subsequent introduction of the Z protective group. The corresponding acid chloride is then prepared as described for Intermediate 7A.

Intermediate 16A

Benzyl[2-(2-chloro-2-oxoethoxy)ethyl](4-methoxybenzyl)carbamate

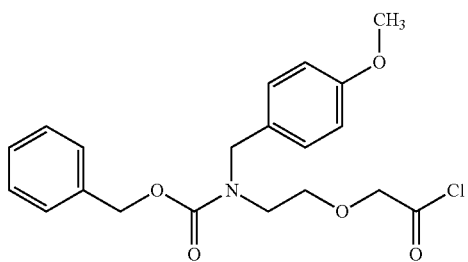

Stage a):

12 g (74.4 mmol) of tert-butyl (2-hydroxyethyl)carbamate are stirred with 43.6 g (223.3 mmol) of tert-butyl bromoacetate in a mixture of 400 ml of toluene and 20 g of concentrated sodium hydroxide solution in the presence of 200 mg (0.59 mmol) of tetrabutylammonium bisulphate at RT for 1 h.

Then a further 15 g of tert-butyl bromoacetate are added, and the mixture is stirred at RT for a further hour. It is then diluted with toluene and water, and the phases are separated. The organic phase is dried and concentrated in vacuo. The residue is mixed with 100 ml of anhydrous trifluoroacetic acid and stirred at RT for 90 min. The gummy residue after concentration is treated with diethyl ether. The gum remaining after decantation is dried under high vacuum. 10.8 g (62% of theory) of the intermediate (2-aminoethoxy)acetic acid are obtained in this way (as trifluoroacetate).

DC (acetonitrile/water/glacial acetic acid 5:1:0.2): $R_f$=0.08.

Stage b):

The amino acid obtained above is then reacted as described for Intermediate 12A to give (2-{[(benzyloxy)carbonyl](4-methoxybenzyl)amino}ethoxy)acetic acid.

Yield: 2.56 g (13% of theory)
HPLC (method 2): $R_t$=5.16 min;
LC-MS (method 12): $R_t$=3.1 min; m/z=374 $(M+H)^+$.

Stage c):

2.56 g (6.86 mmol) of the (2-{[(benzyloxy)carbonyl](4-methoxybenzyl)amino}acetic acid obtained are then reacted as described for Intermediate 12A with thionyl chloride to give the title compound.

Yield: 2.65 g (99% of theory)
HPLC (method 2): $R_t$=5.11 min.

Exemplary Embodiments

General Procedure 2 for Preparing Caesium Salts of Carboxylic Acids or Suitably Protected Amino Acid Derivatives 1 mmol of the appropriate carboxylic acid is dissolved in a mixture of 10 ml of dioxane and 10 ml of water, and 0.5 mmol of caesium carbonate is added. This is followed by lyophilization.

Example 1

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl glycinate hydrochloride

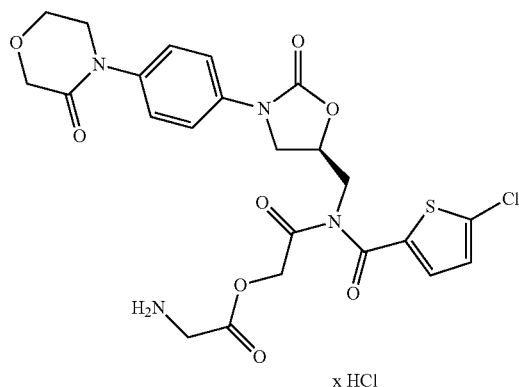

Stage a):

11 mg (21 μmol) of Intermediate 1A are dissolved with 7.9 mg (26 μmol) of the caesium salt of Boc-glycine (prepared from Boc-glycine by General Procedure 2) in 5 ml of DMF. Stirring at RT for 3 h is followed by purification by preparative HPLC (method 1). The appropriate fractions are concentrated and dried under high vacuum.

Yield: 7 mg (50% of theory)
HPLC (method 2): $R_t$=5.2 min;
LC-MS (method 6): $R_t$=2.11 min; m/z=651 $(M+H)^+$.

Stage b):

7 mg (11 μmol) of the protected intermediate obtained above are mixed with 3 ml of a 22% strength solution of hydrogen chloride in dioxane. After 30 min, the mixture is concentrated in vacuo at ≦25° C., and the residue is lyophilized from dioxane.

Yield: 4.5 mg (72% of theory)
HPLC (method 2): $R_t$=4.2 min;
LC-MS (method 5): $R_t$=1.41 min; m/z=551 $(M+H)^+$.

Example 2

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl-2-methylalaninate hydrochloride

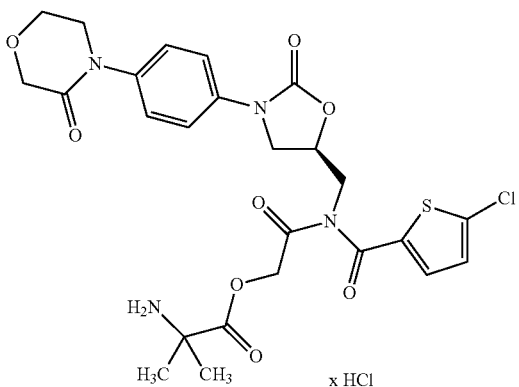

Stage a):

38 mg (74 μmol) of Intermediate 1A are dissolved with 32.3 mg (96 μmol) of the caesium salt of N-Boc-2-methylalanine (prepared from N-Boc-2-methylalanine by General Procedure 2) in 38 ml of DMF. Stirring at RT with ultrasound treatment for 3 h is followed by purification by preparative HPLC (method 1). The appropriate fractions are concentrated and dried under high vacuum.

Yield: 29 mg (58% of theory)
HPLC (method 2): $R_t$=5.38 min;
LC-MS (method 6): $R_t$=2.27 min; m/z=679 $(M+H)^+$.

Stage b):

16.3 mg (24 μmol) of the protected intermediate obtained above are mixed with 3 ml of a 22%-strength solution of hydrogen chloride in dioxane. After 30 min, the mixture is concentrated in vacuo at ≦25° C., and the residue is lyophilized from dioxane.

Yield: 13 mg (88% of theory)
HPLC (method 2): $R_t$=4.3 min;
LC-MS (method 6): $R_t$=1.27 min; m/z=579 $(M+H)^+$.

Example 3

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl L-valinate hydrochloride

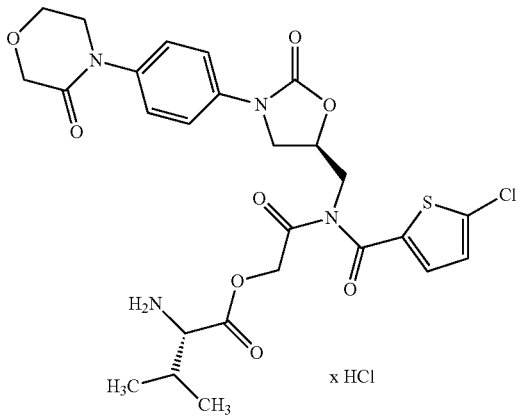

Stage a):

19 mg (37 μmol) of Intermediate 1A are dissolved with 16.8 mg (48 μmol) of the caesium salt of N-Boc-valine (prepared from N-Boc-valine by General Procedure 2) in 10 ml of DMF. Stirring at RT with ultrasound treatment for 1.5 h is followed by purification by preparative HPLC (method 1). The appropriate fractions are concentrated and dried under high vacuum.

Yield: 13.5 mg (53% of theory)
HPLC (method 2): $R_t$=5.45 min;
LC-MS (method 4): $R_t$=2.69 min; m/z=693 (M+H)$^+$.

Stage b):

13.5 mg (19 μmol) of the protected intermediate obtained above are mixed with 3 ml of a 22% strength solution of hydrogen chloride in dioxane. After 30 min, the mixture is concentrated in vacuo at ≦25° C., and the residue is lyophilized from dioxane.

Yield: 12 mg (98% of theory)
HPLC (method 2): $R_t$=4.43 min;
LC-MS (method 5): $R_t$=1.54 min; m/z=593 (M+H)$^+$.

Example 4

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl L-prolinate hydrochloride

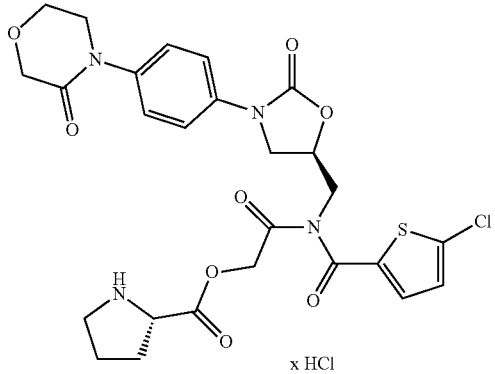

Stage a):

20 mg (39 μmol) of Intermediate 1A are dissolved with 17.6 mg (51 μmol) of the caesium salt of N-Boc-proline (prepared from N-Boc-proline by general procedure 2) in 5 ml of DMF. Stirring at RT with ultrasound treatment for 2 h is followed by purification by preparative HPLC (method 1). The appropriate fractions are concentrated and dried under high vacuum.

Yield: 11.4 mg (42% of theory)
HPLC (method 2): $R_t$=5.44 min;
LC-MS (method 4): $R_t$=2.61 min; m/z=691 (M+H)$^+$.

Stage b):

11.3 mg (16 μmol) of the protected intermediate obtained above are mixed with 2.5 ml of a 22% strength solution of hydrogen chloride in dioxane. After 30 min, the mixture is concentrated in vacuo at ≦25° C., and the residue is lyophilized from dioxane.

Yield: 10 mg (97% of theory)
HPLC (method 2): $R_t$=4.34 min;
LC-MS (method 6): $R_t$=1.26 min; m/z=591 (M+H)$^+$.

Example 5

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl N-methylglycinate hydrochloride

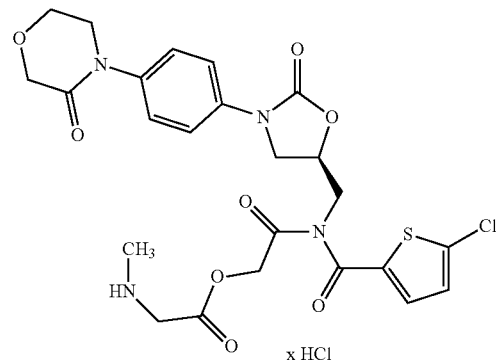

Stage a):

20 mg (39 μmol) of Intermediate 1A are dissolved with 17.5 mg (55 μmol) of the caesium salt of N-Boc-sarcosine (prepared from N-Boc-sarcosine by general procedure 2) in 4 ml of DMF. Stirring at RT with ultrasound treatment for 3 h is followed by purification by preparative HPLC (method 1). The appropriate fractions are concentrated and dried under high vacuum.

Yield: 11 mg (42% of theory)
HPLC (method 2): $R_t$=5.35 min;
LC-MS (method 5): $R_t$=2.43 min; m/z=665 (M+H)$^+$.

Stage b):

11 mg (16 μmol) of the protected intermediate obtained above are mixed with 2 ml of a 22% strength solution of hydrogen chloride in dioxane. After 30 min, the mixture is concentrated in vacuo at ≦25° C., and the residue is lyophilized from dioxane.

Yield: 9.5 mg (96% of theory)
HPLC (method 2): $R_t$=4.24 min;
LC-MS (method 4): $R_t$=1.57 min; m/z=565 (M+H)$^+$.

Example 6

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl D-valinate hydrochloride

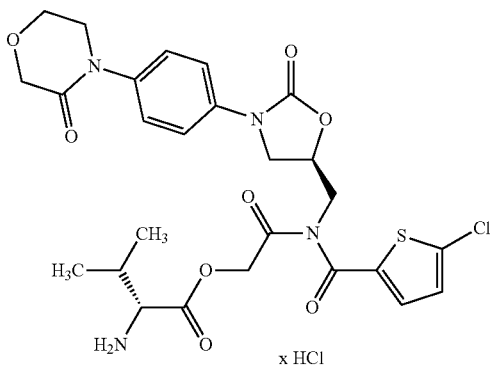

Stage a):

20 mg (40 μmol) of Intermediate 1A are dissolved with 19 mg (55 μmol) of the caesium salt of Boc-D-valine (prepared from Boc-D-valine by General Procedure 2) in 4 ml of DMF. Stirring at RT for 2 h is followed by purification by preparative HPLC (method 1). The appropriate fractions are concentrated and dried under high vacuum.

Yield: 23 mg (85% of theory)
HPLC (method 2): $R_t$=5.6 min;
LC-MS (method 4): $R_t$=2.72 min; m/z=693 (M+H)$^+$.

Stage b):

23 mg (33 μmol) of the protected intermediate obtained above are mixed with 3 ml of a 22% strength solution of hydrogen chloride in dioxane. After 30 min, the mixture is concentrated in vacuo at ≤25° C., and the residue is lyophilized from dioxane.

Yield: 20 mg (96% of theory)
HPLC (method 2): $R_t$=4.5 min;
LC-MS (method 6): $R_t$=1.3 min; m/z=593 (M+H)$^+$.

Example 7

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl L-lysinate dihydrochloride

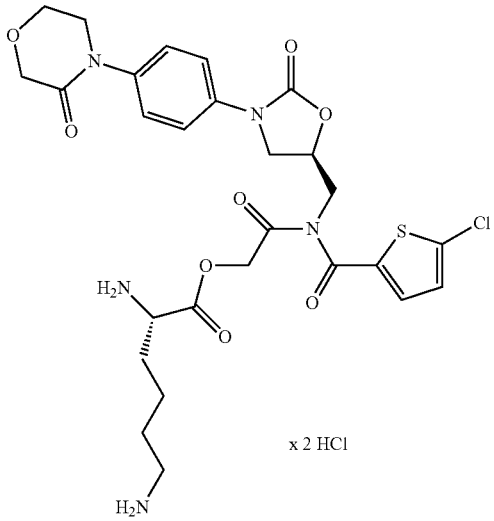

Stage a):

20 mg (40 μmol) of Intermediate 1A are dissolved with 26 mg (55 μmol) of the caesium salt of N,N'-bis-Boc-lysine (prepared from N,N'-bis-Boc-lysine by General Procedure 2) in 4 ml of DMF. Stirring at RT for 2 h is followed by purification by preparative HPLC (method 1). The appropriate fractions are concentrated and dried under high vacuum.

Yield: 14 mg (43% of theory)
HPLC (method 2): $R_t$=5.63 min;
LC-MS (method 5): $R_t$=2.66 min; m/z=822 (M+H)$^+$.

Stage b):

14 mg (17 μmol) of the protected intermediate obtained above are mixed with 2.5 ml of a 22% strength solution of hydrogen chloride in dioxane. After 30 min, the mixture is concentrated in vacuo at ≤25° C., and the residue is lyophilized from dioxane.

Yield: 10 mg (86% of theory)
HPLC (method 2): $R_t$=4.1 min;
LC-MS (method 6): $R_t$=0.92 min; m/z=622 (M+H)$^+$.

Example 8

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl L-histidinate dihydrochloride

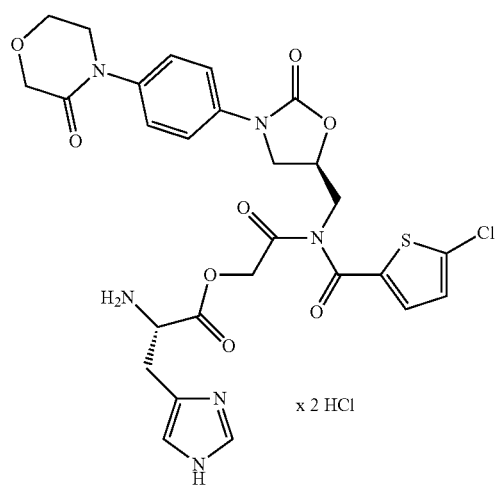

Stage a):

20 mg (40 μmol) of Intermediate 1A are dissolved with 21 mg (55 μmol) of the caesium salt of Boc-L-histidine (prepared from Boc-L-histidine by General Procedure 2) in 4 ml of DMF. Stirring at RT for 2.5 h is followed by removal of the solvent in vacuo. The residue is taken up in acetonitrile/water (1:1) and purified by preparative HPLC (method 1). The appropriate fractions are concentrated and dried under high vacuum.

Yield: 21.9 mg (77% of theory)
HPLC (method 2): $R_t$=4.64 min;
LC-MS (method 5): $R_t$=1.67 min; m/z=731 (M+H)$^+$.

Stage b):

21.9 mg (30 μmol) of the protected intermediate obtained above are mixed with 6 ml of a 22% strength solution of hydrogen chloride in dioxane. After 90 min, the mixture is concentrated in vacuo at ≤25° C. The residue is taken up in acetonitrile/water (1:1) and purified by preparative HPLC (method 1). The appropriate fractions are concentrated and the residue is lyophilized from dioxane.

Yield: 7.2 mg (34% of theory)
HPLC (method 2): $R_t$=4.11 min;
LC-MS (method 6): $R_t$=2.56 min; m/z=631 (M+H)$^+$.

Example 9

2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl D-histidinate dihydrochloride

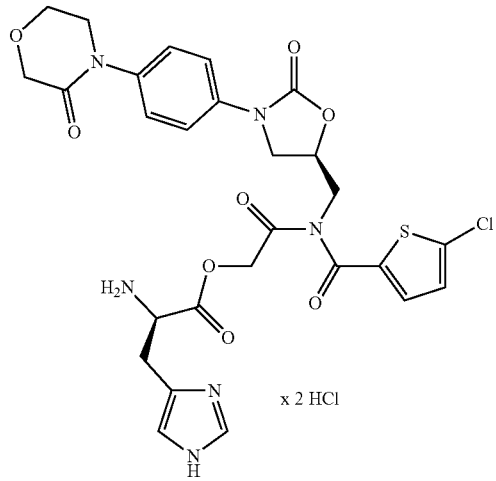

x 2 HCl

Stage a):

25 mg (49 µmol) of Intermediate 1A are dissolved with 26 mg (68 µmol) of the caesium salt of Boc-D-histidine (prepared from Boc-D-histidine by General Procedure 2) in 5 ml of DMF. Stirring at RT for 16 h is followed by removal of the solvent in vacuo. The residue is taken up in acetonitrile/water (1:1) and purified by preparative HPLC (method 1). The appropriate fractions are concentrated and dried under high vacuum.

Yield: 18.3 mg (51% of theory)
HPLC (method 2): $R_t$=4.62 min.

Stage b):

18 mg (25 µmol) of the protected intermediate obtained above are mixed with 2 ml of a 22% strength solution of hydrogen chloride in dioxane. After 4 h, the mixture is concentrated in vacuo at ≦25° C. The residue is taken up in acetonitrile/water (1:1) and purified by preparative HPLC (method 1). The appropriate fractions are concentrated and the residue is lyophilized from dioxane.

Yield: 6 mg (37% of theory)
HPLC (method 2): $R_t$=4.1 min;
LC-MS (method 5): $R_t$=1.15 min; m/z=631 (M+H)⁺.

Example 10

S-{2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl}(2S)-2-amino-3-methylbutanethioate hydrobromide

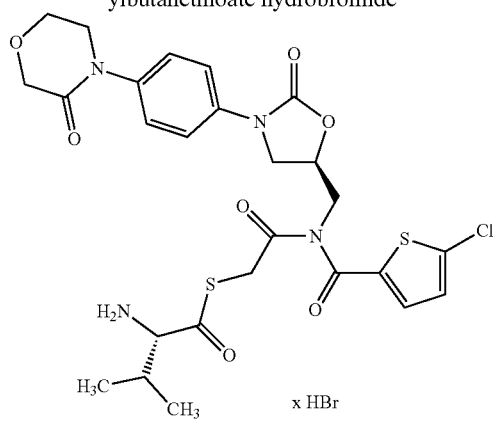

x HBr

Stage a):

(2S)-2-{[(Benzyloxy)carbonyl]amino}-3-methylbutanethioic S-acid

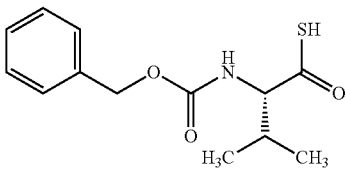

The title compound is prepared from Z-valine in analogy to a procedure known from the literature [R. Michelot et al., *Bioorg. Med. Chem.* 1996, 4, 2201].

Stage b):

200 mg (748 µmol) of (2S)-2-{[(benzyloxy)carbonyl]amino}-3-methylbutanethioic S-acid are taken up in 10 ml of dioxane and 10 ml of water, and 110 mg (337 µmol) of caesium carbonate are added. As soon as a clear solution is produced, it is lyophilized. 300 mg of the caesium salt are obtained in quantitative yield.

27 mg (68 µmol) of this caesium salt and 25 mg (49 µmol) of Intermediate 1A are dissolved in 5 ml of DMF. Stirring at RT for 2 h is followed by removal of the solvent in vacuo. The residue is taken up in acetonitrile/water (1:1) and purified by preparative HPLC (method 1). The appropriate fractions are concentrated and dried under high vacuum.

Yield: 24 mg (66% of theory)
HPLC (method 2): $R_t$=5.62 min;
LC-MS (method 6): $R_t$=2.47 min; m/z=743 (M+H)⁺.

Stage c):

24 mg (32.3 µmol) of the protected intermediate obtained above are mixed with 2 ml of 33% strength solution of hydrogen bromide in glacial acetic acid. After stirring at RT for 1 h, the mixture is concentrated in vacuo at ≦25° C., and the residue is lyophilized from dioxane/water.

Yield: 21 mg (94% of theory)
HPLC (method 2): $R_t$=4.43 min;
LC-MS (method 4): $R_t$=1.63 min; m/z=609 (M+H)⁺.

Example 11

S-{2-[[(5-Chloro-2-thienyl)carbonyl]({(5S)-2-oxo-3-[4-(3-oxomorpholin-4-yl)phenyl]-1,3-oxazolidin-5-yl}methyl)amino]-2-oxoethyl}(2S)-2-amino-3-methylbutanethioate hydrochloride

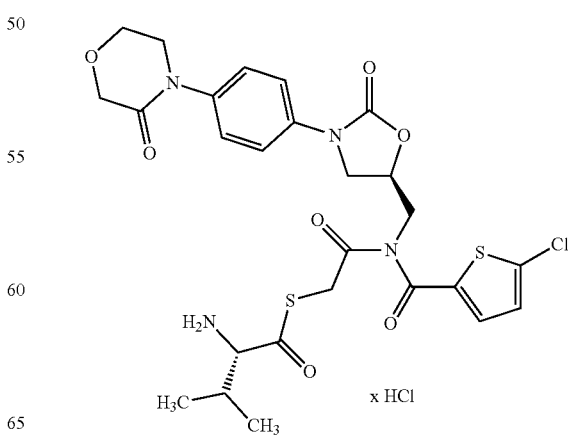

x HCl

Stage a):

(2S)-2-[(tent-Butoxycarbonyl)amino]-3-methylbutanethioic S-acid

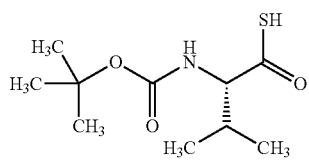

The title compound is prepared from Boc-valine in analogy to a procedure known from the literature [R. Michelot et al., *Bioorg. Med. Chem.* 1996, 4, 2201).

Stage b):

200 mg (857 μmol) of (2S)-2-[(tert-butoxycarbonyl)amino]-3-methylbutanethioic S-acid are taken up in 10 ml of dioxane and 10 ml of water, and 126 mg (386 μmol) of caesium carbonate are added. As soon as a clear solution is produced, it is lyophilized. 310 mg of the caesium salt are obtained in quantitative yield.

25 mg (68 μmol) of this caesium salt and 25 mg (49 μmol) of Intermediate 1A are dissolved in 4 ml of DMF. Stirring at RT for 1 h is followed by removal of the solvent in vacuo. The residue is taken up in acetonitrile/water (1:1) and purified by preparative HPLC (method 1). The appropriate fractions are concentrated and dried under high vacuum.

Yield: 23 mg (65% of theory)
HPLC (method 2): $R_t$=5.64 min;
LC-MS (method 4): $R_t$=2.76 min; m/z=709 (M+H)$^+$.

Stage c):

23 mg (32 μmol) of the protected intermediate obtained above are mixed with 4 ml of a 22% strength solution of hydrogen chloride in dioxane. After stirring at RT for 1 h, the mixture is concentrated in vacuo at ≦25° C., and the residue is lyophilized from dioxane.

Yield: 20 mg (97% of theory)
HPLC (method 2): $R_t$=4.47 min;
LC-MS (method 6): $R_t$=1.35 min; m/z=609 (M+H)$^+$.

Example 12

5-Chloro-N-[4-(methylamino)butanoyl]-N-({(5S)-2-oxo-3-[4-(3-oxomorpholin-4-yl)phenyl]-1,3-oxazolidin-5-yl}methyl)thiophene-2-carboxamide hydrobromide

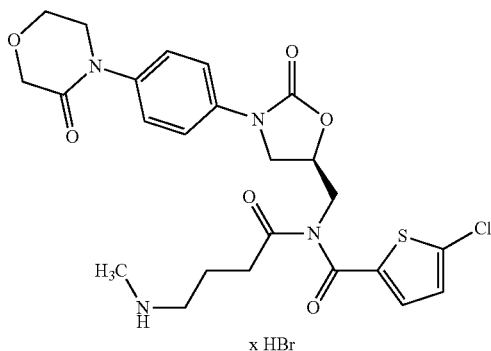

Stage a):

145.4 mg (0.334 mmol) of compound (A) are dissolved in 25 ml of DMF, 24 mg (1 mmol) of sodium hydride are added, and the mixture is stirred at RT for 30 min. Then 1.8 g (6.67 mmol) of Intermediate 7A are added. The mixture is stirred at RT for a further 15 min and then a few drops of water are added. It is then concentrated and the residue is taken up in 300 ml of dichloromethane. Extraction is carried out firstly with water and then three times with 300 ml of a 5% strength sodium bicarbonate solution. The dichloromethane phase is separated off and concentrated. The residue is stirred with a mixture of 15 ml of dichloromethane and 10 ml of diethyl ether. Insolubles are removed by filtration and the remaining solution is concentrated. The residue is purified by preparative HPLC (method 1). The appropriate fractions, which contain a bisacylated by-product produced after enolization of the monoacyl compound, are concentrated and dried under high vacuum. A purer fraction of 41 mg (13.6% of theory) and a slightly impure fraction of 59 mg (19.6% of theory) are obtained and are employed together in the following stage.

HPLC (method 2): $R_t$=6.06 min;
LC-MS (method 5): $R_t$=2.88 min; m/z=902 (M+H)$^+$.

Stage b):

100 mg (0.11 mmol) of the Z-protected intermediate obtained above are taken up in 3.3 ml of glacial acetic acid, and 17 ml of a 33% strength solution of hydrogen bromide in glacial acetic acid are added. Under these conditions there is also cleavage of the enol ester. After stirring at RT for 5 min, conversion to the target compound is complete and the mixture is concentrated under high vacuum. The residue is concentrated from acetonitrile twice and then purified by preparative HPLC.

Yield: 29.6 mg (73.5% of theory)
HPLC (method 2): $R_t$=4.2 min;
LC-MS (method 6): $R_t$=1.19 min; m/z=535 (M+H)$^+$.

Example 13

5-Chloro-N-[4-(methylamino)butanoyl]-N-({(5S)-2-oxo-3-[4-(3-oxomorpholin-4-yl)phenyl]-1,3-oxazolidin-5-yl}methyl)thiophene-2-carboxamide hydrochloride

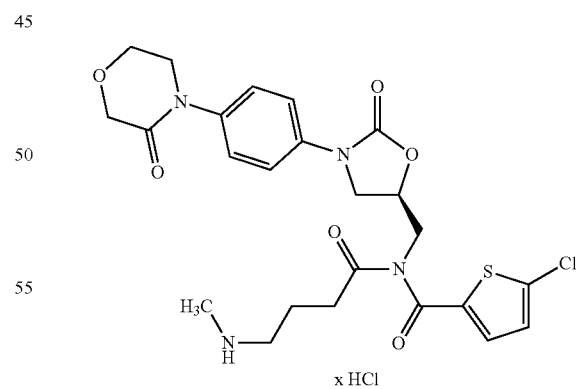

59 mg (0.096 mmol) of the compound from Example 12 are dissolved in 40 ml of acetonitrile/water (1:1), and 1 g (4.8 mmol) of di-tert-butyl pyrocarbonate ("Boc anhydride") is added. Then, 37 μl of N,N-diisopropylethylamine are added in portions, during which a pH of 7.8 is not exceeded. After completion of the reaction after about 15 min, a pH of between 3 and 4 is adjusted with acetic acid, and the mixture is concentrated in vacuo. The residue is taken up in acetonitrile and purified by preparative HPLC (method 1). The appropriate fractions are concentrated and dried in vacuo. 15.5 mg (26% of theory) of the Boc-protected intermediate are obtained. 12.5 mg (0.02 mmol) thereof are then treated with 5 ml of a 22% strength solution of hydrogen chloride in dioxane. After 10 min, the mixture is concentrated in vacuo at ≦25° C. The residue is taken up in water and thoroughly shaken with dichloromethane. The aqueous phase is adjusted to pH 4 with hydrochloric acid and then lyophilized.

Yield: 3.5 mg (31% of theory)
HPLC (method 2): $R_t$=4.24 min;
LC-MS (method 5): $R_t$=1.43 min; m/z=535 (M+H)$^+$.

Example 14

5-Chloro-N-[5-(methylamino)pentanoyl]-N-({(5S)-2-oxo-3-[4-(3-oxomorpholin-4-yl)phenyl]-1,3-oxazolidin-5-yl}methyl)thiophene-2-carboxamide hydrobromide

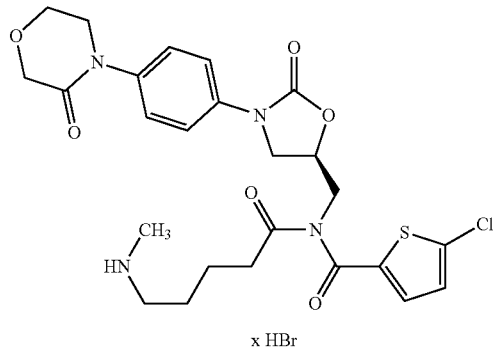

Stage a):
153.6 mg (0.352 mmol) of compound (A) are dissolved in 25 ml of DMF, 25 mg (1 mmol) of sodium hydride are added, and the mixture is stirred at RT for 30 min. Then 2 g (7.05 mmol) of Intermediate 8A, dissolved in 5 ml of DMF, are added. After stirring at RT for a further 15 min, a few drops of water are added to the mixture. It is then concentrated and the residue is taken up in 500 ml of dichloromethane. The solution is extracted twice with 300 ml of a 5% strength sodium bicarbonate solution. The dichloromethane phase is separated off and concentrated. The residue is purified by preparative HPLC (method 1). The appropriate fractions, which contain a bisacylated by-product produced after enolization of the monoacyl compound, are concentrated and dried under high vacuum. 50 mg (15.2% of theory) of a slightly impure fraction are obtained and employed as such in the next stage.
HPLC (method 2): $R_t$=6.23 min.

Stage b):
50 mg (0.027 mmol) of the Z-protected intermediate obtained above are taken up in 1 ml of glacial acetic acid, and 5 ml of a 33% strength solution of hydrogen bromide in glacial acetic acid are added. Under these conditions there is also cleavage of the enol ester. After stirring at RT for 10 min, the reaction to give the target compound is complete and the mixture is concentrated under high vacuum. The residue is concentrated twice from acetonitrile and then purified by repeated preparative HPLC.
Yield: 0.5 mg (3% of theory)
HPLC (method 2): $R_t$=4.32 min;
LC-MS (method 4): $R_t$=1.31 min; m/z=549 (M+H)$^+$.

Example 15

N-Methylglycyl-N-[(5-chloro-2-thienyl)carbonyl]-N$^2$-methyl-N-({(5S)-2-oxo-3-[4-(3-oxomorpholin-4-yl)phenyl]-1,3-oxazolidin-5-yl}methyl)glycinamide hydrobromide

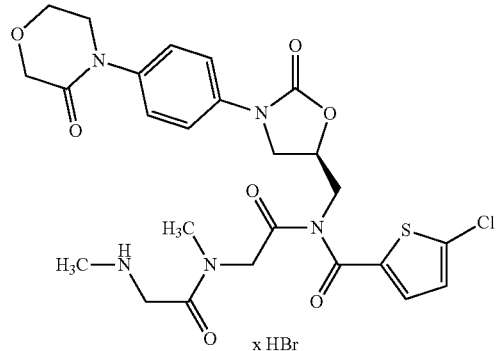

Stage a):
108 mg (0.19 mmol) of Intermediate 2A are dissolved in 25 ml of DMF, 14 mg (0.57 mmol) of sodium hydride are added, and the mixture is stirred at RT for 15 min. Then 534 mg (2.95 mmol) of Intermediate 11A, dissolved in 5 ml of DMF, are added. After stirring at RT for a further 10 min, a few drops of water are added to the mixture. It is then concentrated and the residue is taken up in 500 ml of dichloromethane. The solution is extracted three times with 300 ml of a 5% strength sodium bicarbonate solution. The dichloromethane phase is separated off and concentrated. The residue is purified by preparative HPLC (method 1) twice. The appropriate fractions are concentrated and dried under high vacuum.
Yield: 31 mg (23% of theory)
HPLC (method 2): $R_t$=5.15 min;
LC-MS (method 5): $R_t$=2.28 min; m/z=712 (M+H)$^+$.

Stage b):
31 mg (0.044 mmol) of the Z-protected intermediate obtained above are taken up in 1 ml of glacial acetic acid, and 3 ml of a 33% strength solution of hydrogen bromide in glacial acetic acid are added. Stirring at RT for 45 min is followed by concentration under high vacuum. The residue is purified by repeated preparative HPLC.
Yield: 1 mg (3.3% of theory)
HPLC (method 2): $R_t$=4.23 min;
LC-MS (method 4): $R_t$=1.32 min; m/z=578 (M+H)$^+$.

Example 16

N-Methyl-β-alanyl-N-[(5-chloro-2-thienyl)carbonyl]-N$^2$-methyl-N-({(5S)-2-oxo-3-[4-(3-oxomorpholin-4-yl)phenyl]-1,3-oxazolidin-5-yl}methyl)glycinamide hydrobromide

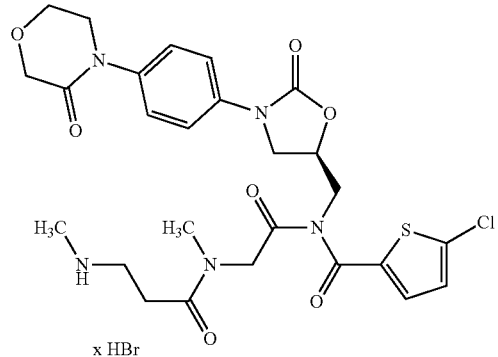

Stage a):

40 mg (0.069 mmol) of Intermediate 6A are dissolved in 10 ml of DMF, 5 mg (0.21 mmol) of sodium hydride are added, and the mixture is stirred at RT for 15 min. Then 249 mg (1.38 mmol) of Intermediate 11A, dissolved in 5 ml of DMF, are added. After stirring at RT for a further 15 min, a few drops of water are added to the mixture. It is then concentrated and the residue is taken up in 500 ml of dichloromethane. The solution is extracted twice with 50 ml of a 5% strength sodium bicarbonate solution. The dichloromethane phase is separated off and concentrated. The residue is purified by preparative HPLC (method 1) twice. The appropriate fractions are concentrated and dried under high vacuum.

Yield: 4.6 mg (9.2% of theory)
HPLC (method 2): $R_t$=5.16 min;
LC-MS (method 6): $R_t$=2.17 min; m/z=726 (M+H)$^+$.

Stage b):

4.2 mg (0.006 mmol) of the Z-protected intermediate obtained above are mixed with 1 ml of a 33% strength solution of hydrogen bromide in glacial acetic acid. Stirring at RT for 30 min is followed by concentration under high vacuum. The residue is taken up in water and extracted with dichloromethane, and the aqueous phase is then lyophilized.

Yield: 2 mg (51% of theory)
HPLC (method 2): $R_t$=4.25 min;
LC-MS (method 6): $R_t$=1.16 min; m/z=592 (M+H)$^+$.

Example 17

5-Chloro-N-[5-(methylamino)pentanoyl]-N-({(5S)-2-oxo-3-[4-(3-oxomorpholin-4-yl)phenyl]-1,3-oxazolidin-5-yl}methyl)thiophene-2-carboxamide hydrochloride

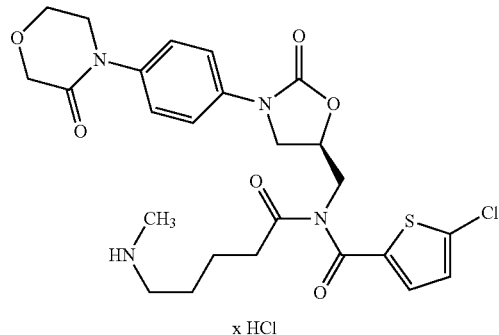

x HCl

Stage a):

1.96 g (4.5 mmol) of compound (A) are dissolved in 70 ml of DMF, 323 mg (13.5 mmol) of sodium hydride are added, and the mixture is stirred for 30 min. Then 5.1 g (18 mmol) of Intermediate 8A, dissolved in 10 ml of DMF, are added. After stirring at RT for a further 15 min, 20 ml of water are added to the mixture. It is then concentrated and the residue is taken up in 500 ml of ethyl acetate. The solution is extracted three times with 300 ml of a 5% strength sodium bicarbonate solution. The ethyl acetate phase is separated off and concentrated. The residue is stirred with 40 ml of a dichloromethane/diethyl ether mixture (2:1) and then filtered. The remaining solution is concentrated in vacuo. The residue is then stirred with 100 ml of a saturated solution of hydrogen chloride in dichloromethane for 2 h, during which the initially produced enol ester is cleaved. The mixture is then concentrated, and the remaining residue is purified by flash chromatography on silica gel with ethyl acetate/toluene 5:1 as eluent. The appropriate fractions are concentrated, and 721 mg (23.5% of theory) of the Z-protected intermediate are obtained.

HPLC (method 2): $R_t$=5.54 min.

Stage b):

720 mg (1.05 mmol) of the Z-protected intermediate obtained above are stirred in 20 ml of anhydrous trifluoroacetic acid overnight. The mixture is then concentrated under high vacuum, keeping the temperature at about 20° C. The residue is taken up in 100 ml of hydrochloric acid adjusted to pH 3, and extracted twice each with 100 ml of dichloromethane and 100 ml of ethyl acetate. The aqueous phase is concentrated and the residue is purified by preparative HPLC. Concentration of the appropriate fractions and lyophilization from hydrochloric acid (pH 3) results in the target compound.

Yield: 20 mg (3.3% of theory)
HPLC (method 2): $R_t$=4.29 min;
LC-MS (method 5): $R_t$=1.27 min; m/z=549 (M+H)$^+$.

Example 18

5-Chloro-N-[6-(methylamino)hexanoyl]-N-({(5S)-2-oxo-3-[4-(3-oxomorpholin-4-yl)phenyl]-1,3-oxazolidin-5-yl}methyl)thiophene-2-carboxamide hydrochloride

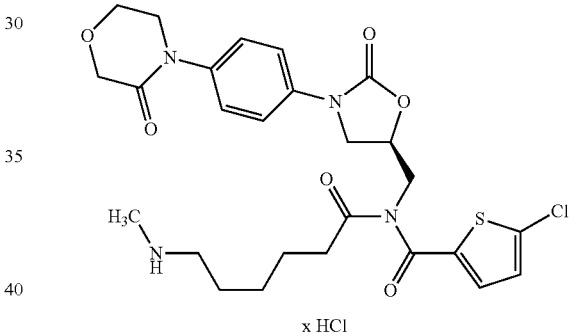

x HCl

Stage a):

2 g (4.59 mmol) of compound (A) are dissolved in 70 ml of DMF, 330 mg (13.8 mmol) of sodium hydride are added, and the mixture is stirred at RT for 30 min. Then 5.1 g (18 mmol) of Intermediate 10A, dissolved in 10 ml of DMF, are added. After stirring at RT for a further 15 min, 20 ml of water are added to the mixture. It is then concentrated and the residue is stirred with 100 ml of a saturated solution of hydrogen chloride in dichloromethane for 2 h, during which the initially produced enol ester is cleaved. The mixture is then concentrated, and the residue is taken up in 600 ml of ethyl acetate. The solution is extracted three times with a 10% strength sodium carbonate solution. The ethyl acetate phase is separated off and concentrated. The residue is stirred with 150 ml of a dichloromethane/diethyl ether mixture (2:1) and then filtered. The remaining solution is concentrated in vacuo and the residue is purified by flash chromatography on silica gel with ethyl acetate/toluene 5:1 as eluent. The appropriate fractions are concentrated, resulting in the still slightly impure product. Purification again by flash chromatography on silica gel with acetonitrile/dichloromethane 1:1 as eluent then leads to 572 mg (18% of theory) of the purer Z-protected intermediate.

HPLC (method 2): $R_t$=5.68 min.

Stage b):

572 mg (0.82 mmol) of the intermediate obtained above are treated in 50 ml of anhydrous trifluoroacetic acid in an ultrasonic bath for 6 h. The mixture is then concentrated under high vacuum, keeping the temperature at about 20° C. The residue is taken up in 100 ml of hydrochloric acid adjusted to pH 3 and filtered. The aqueous phase is concentrated and the residue is purified by preparative HPLC. Concentration of the appropriate fractions and lyophilization from hydrochloric acid (pH 3) results in 283 mg (58% of theory) of the target compound.

HPLC (method 2): $R_t$=4.35 min;
LC-MS (method 6): $R_t$=1.24 min; m/z=563 (M+H)$^+$.

Example 19

N-(4-Aminobutanoyl)-5-chloro-N-({(5S)-2-oxo-3-[4-(3-oxomorpholin-4-yl)phenyl]-1,3-oxazolidin-5-yl}methyl)thiophene-2-carboxamide hydrochloride

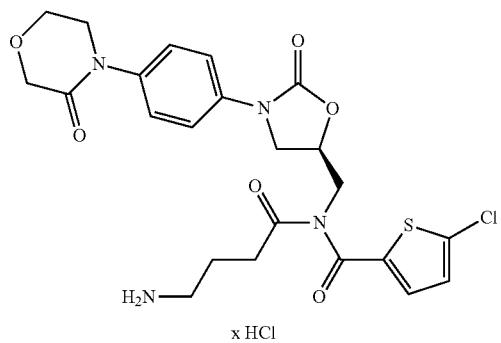

x HCl

Stage a):

1.33 g (3.06 mmol) of compound (A) are dissolved in 75 ml of DMF, 220 mg (9.2 mmol) of sodium hydride are added, and the mixture is stirred at RT for 30 min. Then 11.5 g (30.6 mmol) of Intermediate 14A, dissolved in 10 ml of DMF, are added. After stirring at RT for a further 15 min, 20 ml of water are added to the mixture. It is then concentrated and the residue is taken up in 300 ml of ethyl acetate. The solution is extracted three times with 300 ml of a 10% strength sodium carbonate solution. The organic phase is separated off and concentrated, and the residue is taken up in 50 ml of dichloromethane. After brief stirring, insoluble constituents are filtered off, and the dichloromethane phase is concentrated. The residue is purified by flash chromatography on silica gel with ethyl acetate/toluene 5:1 as eluent. The product-containing fractions, which contain a bisacylated by-product (m/z=1113), are concentrated. The residue is then stirred with 10 ml of a saturated solution of hydrogen chloride in dichloromethane for 2 h, during which the initially produced enol ester is cleaved. The mixture is then concentrated, and the remaining residue is again purified by flash chromatography on silica gel with ethyl acetate/toluene 5:1 as eluent. The appropriate fractions are concentrated, and 151 mg (7% of theory) of the diprotected intermediate are obtained.

HPLC (method 2): $R_t$=5.83 min;
LC-MS (method 6): $R_t$=2.61 min; m/z=775 (M+H)$^+$.

Stage b):

151 mg (0.2 mmol) of the intermediate obtained above are stirred in 8 ml of anhydrous trifluoroacetic acid at RT overnight. The mixture is then concentrated under high vacuum, keeping the temperature at about 20° C. The residue is taken up in 100 ml of hydrochloric acid adjusted to pH 3, and extracted with 75 ml of dichloromethane and then twice with ethyl acetate. The aqueous phase is concentrated and the residue is lyophilized from hydrochloric acid (pH 3).

Yield: 70 mg (64% of theory)
HPLC (method 2): $R_t$=4.13 min;
LC-MS (method 5): $R_t$=1.38 min; m/z=521 (M+H)$^+$.

Example 20

N-(5-Aminopentanoyl)-5-chloro-N-({(5S)-2-oxo-3-[4-(3-oxomorpholin-4-yl)phenyl]-1,3-oxazolidin-5-yl}methyl)thiophene-2-carboxamide hydrochloride

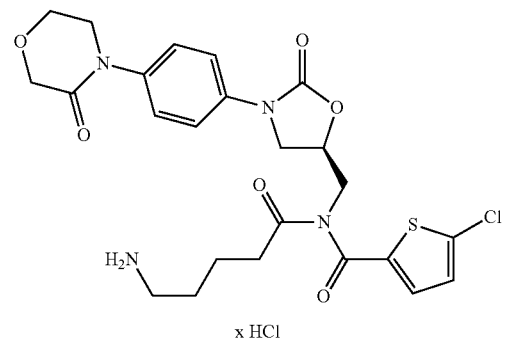

x HCl

Stage a):

2.83 g (6.5 mmol) of compound (A) are dissolved in 100 ml of DMF, 468 mg (19.5 mmol) of sodium hydride are added, and the mixture is stirred at RT for 30 min. Then 7.6 g (19.5 mmol) of Intermediate 12A, dissolved in 10 ml of DMF, are added. After stirring at RT for a further 15 min, 20 ml of water are added to the mixture. It is then concentrated and the residue is stirred with 150 ml of a saturated solution of hydrogen chloride in dichloromethane for 1 h, during which the initially produced enol ester is cleaved. The mixture is then concentrated and the residue is taken up in 700 ml of ethyl acetate. The solution is extracted twice with 200 ml of a 10% strength sodium carbonate solution each time. The organic phase is separated off and concentrated, and the residue is taken up in 30 ml of ethyl acetate and 30 ml of diethyl ether. After brief stirring, insoluble constituents are filtered off and the organic phase is concentrated. The residue is purified by flash chromatography on silica gel with ethyl acetate/toluene 4:1 as eluent. The appropriate fractions are concentrated and the residue is taken up in 10 ml ethyl acetate. 100 ml of cold diethyl ether are added, and the mixture is left to stand at 0° C. for 30 min. The residue after filtration is treated again with 100 ml of diethyl ether. After filtration again, the residue is collected and dried. 1 g (20% of theory) of the diprotected intermediate are obtained.

HPLC (method 2): $R_t$=5.92 min;
LC-MS (method 6): $R_t$=2.68 min; m/z=789 (M+H)$^+$.

Stage b):

1 g (1.3 mmol) of the resulting intermediate are treated in 70 ml of anhydrous trifluoroacetic acid in an ultrasonic bath for 6 h. The mixture is then concentrated under high vacuum, keeping the temperature at about 20° C. The residue is taken up in 350 ml of hydrochloric acid adjusted to pH 3 and, after stirring at RT for 15 minutes, extracted with 100 ml of dichloromethane. The aqueous phase is separated off and then extracted again with 100 ml of ethyl acetate. The aqueous phase is separated off, then briefly distilled under high vacuum to remove remaining ethyl acetate, and finally lyophilized.

Yield: 586 mg (81% of theory)
HPLC (method 2): $R_t$=4.2 min;
LC-MS (method 6): $R_t$=1.17 min; m/z=535 (M+H)$^+$.

Example 21

N-(6-Aminohexanoyl)-5-chloro-N-({(5S)-2-oxo-3-[4-(3-oxomorpholin-4-yl)phenyl]-1,3-oxazolidin-5-yl}methyl)thiophene-2-carboxamide hydrochloride

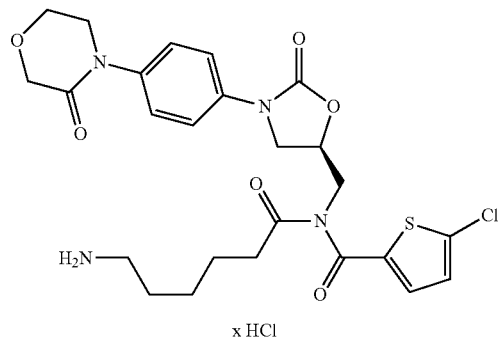

Stage a):

1.6 g (3.7 mmol) of compound (A) are dissolved in 50 ml of DMF, 263 mg (11 mmol) of sodium hydride are added, and the mixture is stirred at RT for 30 min. Then 14.1 g (36.6 mmol) of intermediate 13A, dissolved in 10 ml of DMF, are added. After stirring at RT for a further 15 min, 20 ml of water are added to the mixture. It is concentrated and the residue is taken up in 500 ml of ethyl acetate. The solution is extracted three times with 100 ml of a 10% strength sodium carbonate solution each time. The organic phase is separated off and concentrated, and the residue is taken up in 15 ml of dichloromethane/diethyl ether (2:1). After brief stirring, insoluble constituents are filtered off, and the organic phase is concentrated. The residue is purified by flash chromatography on silica gel with ethyl acetate/toluene 5:1 as eluent. 256 mg (9% of theory) of the diprotected intermediate are obtained.

HPLC (method 2): $R_t$=6.07 min;
LC-MS (method 5): $R_t$=2.92 min; m/z=803 (M+H)$^+$.

Stage b):

256 mg (0.32 mmol) of the intermediate obtained above are stirred in 10 ml of anhydrous trifluoroacetic acid at room temperature overnight. The mixture is then concentrated under high vacuum, keeping the temperature at about 20° C. The residue is taken up in 100 ml of hydrochloric acid adjusted to pH 3 and, after stirring at RT for 15 minutes, extracted with 100 ml of dichloromethane. The aqueous phase is separated off and then extracted again with 100 ml of ethyl acetate. The aqueous phase is concentrated and the residue is purified by preparative HPLC. The appropriate fractions are concentrated and the residue is lyophilized from hydrochloric acid (pH 3).

Yield: 29 mg (16% of theory)
HPLC (method 2): $R_t$=4.28 min;
LC-MS (method 6): $R_t$=1.24 min; m/z=549 (M+H)$^+$.

Example 22

N-[4-(Butylamino)butanoyl]-5-chloro-N-({(5S)-2-oxo-3-[4-(3-oxomorpholin-4-yl)phenyl]-1,3-oxazolidin-5-yl}methyl)thiophene-2-carboxamide hydrochloride

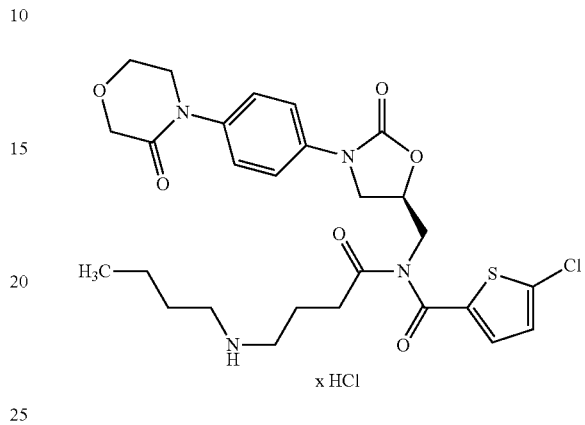

Stage a):

3.215 g (7.38 mmol) of compound (A) are dissolved in 60 ml of DMF, 531 mg (22.1 mmol) of sodium hydride are added, and the mixture is stirred at RT for 30 min. Then 6.9 g (22.1 mmol) of Intermediate 15A, dissolved in 10 ml of DMF, are added. After stirring at RT for a further 10 min, 10 ml of water are added to the mixture. It is then concentrated, and the residue is stirred with 70 ml of a saturated solution of hydrogen chloride in dichloromethane overnight, during which the initially produced enol ester is cleaved. The mixture is filtered, and the remaining solution is concentrated. The residue is taken up in 600 ml of ethyl acetate and extracted three times with 100 ml of a 10% strength sodium carbonate solution and once with water. The ethyl acetate phase is separated off and concentrated. The residue is purified by flash chromatography on silica gel with acetonitrile/dichloromethane 1:1 as eluent. The appropriate fractions are concentrated. The remaining resinous product is taken up 20 ml of ethyl acetate, and 40 ml of cold diethyl ether are added. The residue remaining after filtration is washed with diethyl ether. Drying under high vacuum results in 1.7 g (32.4% of theory) of the Z-protected intermediate.

HPLC (method 2): $R_t$=6.0 min;
LC-MS (method 12): $R_t$=3.9 min; m/z=711 (M+H)$^+$.

Stage b):

1.7 g (2.39 mmol) of the protected intermediate are taken up in 50 ml of anhydrous trifluoroacetic acid and treated with ultrasound for 5 h. The mixture is then concentrated under high vacuum, keeping the temperature at about 20° C. The residue is taken up in 200 ml of hydrochloric acid adjusted to pH 3, and extracted three times with 25 ml of ethyl acetate. The aqueous phase is lyophilized and then taken up again in hydrochloric acid (pH 3), filtered and lyophilized again.

Yield: 450 mg (31% of theory)
HPLC (method 2): $R_t$=4.57 min;
LC-MS (method 13): $R_t$=2.81 min; m/z=577 (M+H)$^+$.

Example 23

N-[(2-Aminoethoxy)acetyl]-5-chloro-N-({(5S)-2-oxo-3-[4-(3-oxomorpholin-4-yl)phenyl]-1,3-oxazolidin-5-yl}methyl)thiophene-2-carboxamide hydrochloride

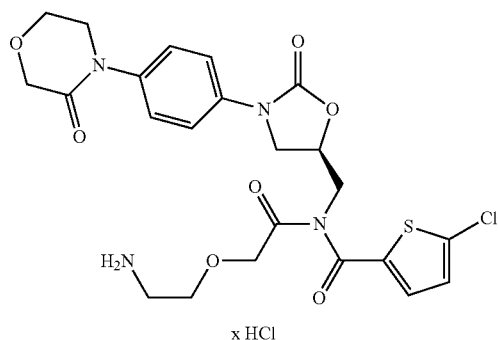

Stage a):

589.6 mg (1.35 mmol) of compound (A) are dissolved in 25 ml of DMF, 97 mg (4 mmol) of sodium hydride are added, and the mixture is stirred at RT for 30 min. Then 2.65 g (6.76 mmol) of Intermediate 16A, dissolved in 4 ml of DMF, are added. After stirring at RT for a further 10 min, 5 ml of water are added to the mixture. It is then concentrated and the residue is stirred with 150 ml of a saturated solution of hydrogen chloride in dichloromethane overnight. It is then concentrated again, and the residue is taken up in 200 ml of ethyl acetate. The solution is extracted twice with 50 ml of a 10% strength sodium carbonate solution each time. The organic phase is separated off and concentrated and the residue is stirred with 30 ml of ethyl acetate. Insoluble constituents are filtered off, and the organic phase is concentrated. The residue is purified by flash chromatography on silica gel with acetonitrile/dichloromethane 1:1 as eluent. The product-containing fractions are concentrated and the residue is again purified by preparative HPLC (method 1). The appropriate fractions are concentrated and dried. 30 mg (3% of theory) of the diprotected intermediate are obtained.

HPLC (method 2): $R_t$=5.71 min;
LC-MS (method 12): $R_t$=3.74 min; m/z=791 (M+H)$^+$.

Stage b):

30 mg (0.038 mmol) of the protected intermediate are stirred in 50 ml of anhydrous trifluoroacetic acid overnight. The mixture is then concentrated under high vacuum, keeping the temperature at about 20° C. The residue is taken up in 30 ml of hydrochloric acid adjusted to pH 3, and 20 ml of dichloromethane are added to the mixture. The phases are separated and the aqueous phase is again extracted with 20 ml of dichloromethane and subsequently with 20 ml of ethyl acetate. The aqueous phase is separated off, then briefly distilled under high vacuum to remove remaining ethyl acetate, and finally lyophilized.

Yield: 17 mg (78% of theory)
HPLC (method 2): $R_t$=4.14 min;
LC-MS (method 12): $R_t$=1.67 min; m/z=537 (M+H)$^+$.

B. DETERMINATION OF SOLUBILITY, STABILITY AND LIBERATION BEHAVIOUR a) Determination of the Solubility:

The test substance is suspended in water or dilute hydrochloric acid (pH 4). This suspension is shaken at room temperature for 24 h. After ultracentrifugation at 224 000 g for 30 min, the supernatant is diluted with DMSO and analysed by HPLC. A two-point calibration plot of the test compound in DMSO is used for quantification.

HPLC Method:

Agilent 1100 with DAD (G1315A), quat. pump (G1311A), autosampler CTC HTS PAL, degasser (G1322A) and column thermostat (G1316A); column. Zorbax Extend-C18 3.5µ; temperature: 40° C.; eluent A: water+5 ml of perchloric acid/litre, eluent B: acetonitrile; flow rate: 0.7 ml/min; gradient: 0-0.5 min 98% A, 2% B; ramp 0.5-4.5 min 10% A, 90% B; 4.5-6 min 10% A, 90% B; ramp 6.5-6.7 min 98% A, 2% B; 6.7-7.5 min 98% A, 2% B.

The solubilities of representative exemplary embodiments in dilute hydrochloric acid (pH 4) are shown in Table 1:

TABLE 1

| Example No. | Solubility [mg/liter] |
|---|---|
| 1 | 320 |
| 2 | >500 |
| 3 | 340 |
| 4 | 480 |
| 5 | 330 |
| 6 | 860 |
| 7 | 340 |
| 10 | 680 |
| 11 | 960 |
| 12 | 350 |

No decomposition of the exemplary compounds in these solutions is observed.

The solubility of the underlying active substance [compound (A)] in dilute hydrochloric acid (pH 4) is determined in this test to be 8.1 mg/litre.

The solubility found for the compound of Example 13 in 5% dextrose adjusted to pH 4 with hydrochloric acid is 2.70 g/litre; the solubilities measured for the compounds of Examples 20, 21 and 22 are above 3 g/litre.

b) Stability in Buffer at Various pH Values:

0.3 mg of the test substance is weighed into a 2 ml HPLC vial and 0.5 ml of acetonitrile is added. The substance is dissolved by putting the sample vessel in an ultrasonic bath for about 10 seconds. Then 0.5 ml of the respective buffer solution is added, and the sample is again treated in the ultrasonic bath.

Buffer Solutions Employed:

pH 4.0: 1 litre of Millipore water is adjusted to pH 4.0 with 1 N hydrochloric acid;

pH 7.4: 90 g of sodium chloride, 13.61 g of potassium dihydrogen phosphate and 83.35 g of 1 M sodium hydroxide solution are made up to 1 litre with Millipore water and then diluted 1:10.

5 µl portions of the test solution are analysed by HPLC for their content of unchanged test substance every hour over a period of 24 hours at 37° C. The percentage areas of the appropriate peaks are used for quantification.

HPLC Method:

Agilent 1100 with DAD (G1314A), binary pump (G1312A), autosampler (G1329A), column oven (G1316A), thermostat (G1330A); column: Kromasil 100 C18, 125 mm×4.6 mm, 5 µm; column temperature: 30° C.; eluent A: water+5 ml of perchloric acid/litre, eluent B: acetonitrile. Gradient 1:

0-1.0 min 98% A, 2% B→1.0-13.0 min 50% A, 50% B→13.0-17.0 min 10% A, 90% B→17.0-18.0 min 10% A, 90% B→18.0-19.5 98% A, 2% B→19.5-23.0 min 98% A, 2% B; flow rate: 2.0 ml/min; UV detection: 210 nm.

Gradient 2:

0-3.0 min 78% A, 22% B→3.0-15.0 min 78% A, 22% B→15.0-17.0 min 10% A, 90% B→17.0-18.0 min 10% A, 90% B→18.0-20.0 98% A, 2% B→20.0-23.0 min 98% A, 2% B; flow rate: 2.0 ml/min; UV detection: 210 nm.

Gradient 3:

0-3.0 min 70% A, 30% B→3.0-15.0 min 70% A, 30% B→15.0-17.0 min 10% A, 90% B→17.0-18.0 min 10% A, 90% B→18.0-20.0 98% A, 2% B→20.0-23.0 min 98% A, 2% B; flow rate: 2.0 ml/min; UV detection: 210 nm.

The ratios of the peak areas (F) at the respective time points in relation to the peak areas at the starting time are shown in Table 2 for representative exemplary embodiments:

TABLE 2

| Example No. | Buffer pH | % test substance after 4 h [F(t = 4 h) × 100/ F(t = 0 h)] | % Test substance after 24 h [F(t = 24 h) × 100/ F(t = 0 h)] |
| --- | --- | --- | --- |
| 1 | 4 | 100 | 99 |
| 1 | 7.4 | 49 | 3 |
| 2 | 4 | 100 | 100 |
| 2 | 7.4 | 96 | 80 |
| 3 | 4 | 100 | 99 |
| 3 | 7.4 | 88 | 48 |
| 4 | 4 | 100 | 100 |
| 4 | 7.4 | 31 | 0 |
| 5 | 4 | 100 | 94 |
| 5 | 7.4 | 68 | 14 |
| 6 | 4 | 100 | 98 |
| 6 | 7.4 | 90 | 59 |
| 7 | 4 | 100 | 99 |
| 7 | 7.4 | 48 | 3 |
| 8 | 4 | 99 | 81 |
| 8 | 7.4 | 2 | 0 |
| 10 | 4 | 100 | 99 |
| 10 | 7.4 | 8 | 0 |
| 11 | 4 | 100 | 99 |
| 11 | 7.4 | 10 | 0 |
| 12 | 4 | 100 | 98 |
| 12 | 7.4 | 0 | 0 |
| 13 | 4 | 99 | 91 |
| 14 | 4 | 57 | 0 |
| 14 | 7.4 | 0 | 0 |
| 17 | 4 | 83 | 55 |
| 18 | 4 | 100 | 99 |
| 19 | 4 | 100 | 97 |
| 19 | 7.4 | 0 | 0 |
| 20 | 4 | 98 | 90 |
| 20 | 7.4 | 0 | 0 |
| 21 | 4 | 100 | 100 |
| 21 | 7.4 | 92 | 66 |
| 22 | 4 | 100 | 98 |

In this test there is found to be at pH 7.4 a simultaneous increase in the active ingredient compound (A) with the decrease in the content of test substance.

c) In Vitro Stability in Rat Plasma (HPLC Detection):

1 mg of substance is dissolved in 1.25 ml of dimethyl sulphoxide. Then 1.25 ml of water are added. 500 µl of this sample solution are mixed with 500 µl of rat plasma at 37° C. and shaken. A first sample (10 µl) is immediately taken for HPLC analysis. In the period up to 2 h after the start of incubation, further aliquots are taken after 2, 5, 10, 30, 60 and 90 min, and the content of the respective test substance and of the active ingredient compound (A) liberated therefrom is determined HPLC Method:

Agilent 1100 with DAD (G1314A), binary pump (G1312A), autosampler (G1329A), column oven (G1316A), thermostat (G1330A); column: Kromasil 100 C18, 250 mm×4.6 mm, 5 µm; column temperature: 30° C.; eluent A: water+5 ml of perchloric acid/litre, eluent B: acetonitrile.

Gradient:

0-0.5 min 98% A, 2% B→0.5-3.0 min 73% A, 27% B→3.0-18.0 min 73% A, 27% B→18.0-20.0 min 10% A, 90% B→20.0-21.0 90% A, 10% B→21.0-22.5 min 98% A, 2% B→22.5-25.0 min 98% A, 2% B; flow rate: 2.0 ml/min; UV detection: 248 nm.

Result:

The compounds of Examples 13, 17, 20, 22 and 23 are degraded in this test with a half-life of less than 2 min to liberate the active ingredient compound (A).

d) In Vitro Stability in Rat and Human Plasma (LC/MS-MS Detection):

A defined plasma volume (e.g. 2.0 ml) is warmed to 37° C. in a closed test tube in a waterbath. After the intended temperature is reached, a defined amount of the test substance is added as solution (volume of the solvent not more than 2% of the plasma volume). The plasma is shaken and a first sample (50-100 µl) is immediately taken. Then 4-6 further aliquots are taken in the period up to 2 h after the start of incubation.

Acetonitrile is added to the plasma samples to precipitate proteins. After centrifugation, the test substance and, where appropriate, known cleavage products of the test substance in the supernatant are determined quantitatively with a suitable LC/MS-MS method.

Determinations of stability in heparinized rat or human blood are carried out as described for plasma.

The concentrations c of the compound of Example 6 and of the active ingredient compound (A) liberated therefrom determined at various times in the plasma of Wistar rats are shown in Table 3:

TABLE 3

| Incubation time [h] | c [mg/liter] of Example 6 | c [mg/liter] of compound (A) |
| --- | --- | --- |
| 0 | 0.403 | 0.0789 |
| 0.08 | 0.0756 | 0.155 |
| 0.17 | 0.0079 | 0.175 |
| 0.5 | n.d. | 0.178 |
| 1 | n.d. | 0.186 |
| 2 | n.d. | 0.187 |

The concentrations c of the compound of Example 13 and of the active ingredient compound (A) liberated therefrom determined at various times in the plasma of Wistar rats are shown in Table 4:

TABLE 4

| Incubation time [h] | c [mg/liter] of Example 13 | c [mg/liter] of compound (A) |
| --- | --- | --- |
| 0 | 0.5 | 0.178 |
| 0.08 | n.d. | 0.237 |
| 0.17 | n.d. | 0.247 |
| 0.5 | n.d. | 0.257 |
| 1 | n.d. | 0.275 | n.d. = not determinable (below the limit of detection).

e) i.v. Pharmacokinetics in Wistar Rats:

On the day before administration of the substance, a catheter for obtaining blood is implanted in the jugular vein of the experimental animals (male Wistar rats, body weight 200-250 g) under Isofluran® anaesthesiat.

On the day of the experiment, a defined dose of the test substance is administered as solution into the tail vein using a Hamilton® glass syringe (bolus administration, duration of administration <10 s). Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life) and CL (clearance).

f) Hepatocyte Assay to Determine the Metabolic Stability:

The metabolic stability of the test compounds in the presence of hepatocytes is determined by incubating the compounds at low concentrations (preferably below 1 µM) and with low cell counts (preferably with $1\times10^6$ cells/ml) in order to ensure as far as possible linear kinetic conditions in the experiment. Seven samples of the incubation solution are taken in a fixed time pattern for the LC-MS analysis in order to determine the half-life (i.e. the degradation) of the compound. Various clearance parameters (CL) and $F_{max}$ values are calculated from this half-life (see below).

The CL and $F_{max}$ values represent a measure of the phase 1 and phase 2 metabolism of the compound in the hepatocytes. In order to minimize the influence of the organic solvent on the enzymes in the incubation mixtures, this concentration is generally limited to 1% (acetonitrile) or 0.1% (DMSO).

A cell count for hepatocytes in the liver of $1.1\times10^8$ cells/g of liver is used for calculation for all species and breeds. CL parameters calculated on the basis of half-lives extending beyond the incubation time (normally 90 minutes) can be regarded only as rough guidelines.

The calculated parameters and their meaning are:

$F_{max}$ well-stirred [%] maximum possible bioavailability after oral administration Calculation:$(1-CL_{blood}$ well-stirred$/QH)*100$ $CL_{blood}$ well-stirred [L/(h*kg)] calculated blood clearance (well stirred model)

Calculation:$(QH*CL'_{intrinsic})/(QH+CL'_{intrinsic})$ $CL'_{intrinsic}$ [ml/(min*kg)] maximum ability of the liver (of the hepatocytes) to metabolize a compound (on the assumption that the hepatic blood flow is not rate-limiting)

Calculation:$CL'_{intrinsic,apparent}\times$species-specific hepatocyte count$[1.1\times10^8$/g of liver$]\times$species-specific liver weight[g/kg]

$CL'_{intrinsic,apparent}$ [ml/(min*mg)] normalizes the elimination constant by dividing it by the cell count of hepatocytes employed x $(x*10^6/ml)$ Calculation:$k_{el}$[l/min]/(cell count$[x*10^6]$/incubation volume[ml])

(QH=species-specifier hepatic blood flow).

g) Determination of the Antithrombotic Effect in an Arteriovenous Shunt Model in Rats:

Fasting male rats (strain: HSD CPB:WU) are anaesthetized by intraperitoneal administration of a Rompun/Ketavet solution (12 mg/kg/50 mg/kg). Thrombus formation is induced in an arteriovenous shunt based on the method described by P. C. Wong et al. [*Thrombosis Research* 83 (2), 117-126 (1996)]. For this purpose, the left jugular vein and the right carotid artery are exposed. An 8 cm-long polyethylene catheter (PE60, from Becton-Dickinson) is secured in the artery, followed by a 6 cm-long Tygon tube (R-3606, ID 3.2 mm, from Kronlab) which contains a roughened nylon loop (60×0.26 mm, from Berkley Trilene) made into a double loop to produce a thrombogenic surface. A 2 cm-long polyethylene catheter (PE60, from Becton-Dickinson) is secured in the jugular vein and connected by a 6 cm-long polyethylene catheter (PE160, from Becton-Dickinson) to the Tygon tube. The tubes are filled with physiological saline before the shunt is opened. The extracorporeal circulation is maintained for 15 min. The shunt is then removed and the nylon thread with the thrombus is immediately weighed. The empty weight of the nylon thread has been found before the start of the experiment. The test substance (as solution in physiological saline adjusted to pH 4 with 0.1 N hydrochloric acid) is administered as bolus injection before attaching the extracorporeal circulation.

C. EXEMPLARY EMBODIMENTS OF PHARMACEUTICAL COMPOSITIONS

The compounds according to the invention can be converted for example into pharmaceutical preparations in the following way:

i.v. Solution:

The compound according to the invention is dissolved in a concentration below the saturation solubility in a physiologically tolerated solvent (e.g. isotonic saline, 5% glucose solution and/or 30% PEG 400 solution, each of which is adjusted to a pH of 3-5). The solution is sterilized by filtration where appropriate and/or dispensed into sterile and pyrogen-free injection containers.

The invention claimed is:

1. A pharmaceutical composition comprising (a) a compound of the formula (I)

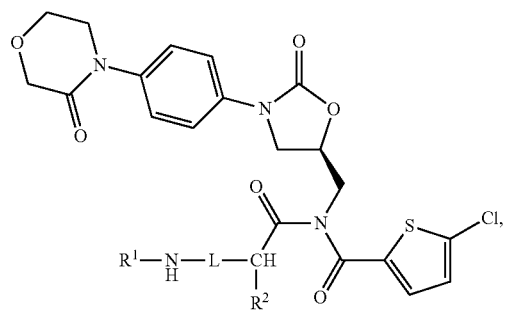

(I)

in which $R^1$ is hydrogen or $(C_1$-$C_4)$-alkyl which may be substituted by hydroxy or $(C_1$-$C_4)$-alkoxy, $R^2$ is hydrogen or $(C_1$-$C_4)$-alkyl, and L is a $(C_1$-$C_4)$-alkanediyl group in which one $CH_2$ group may be replaced by an O atom, or is a group of the formula

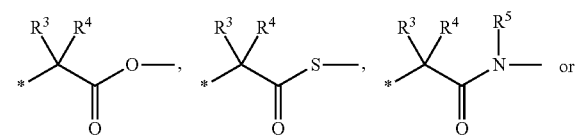

or

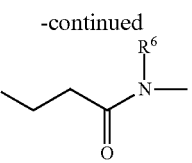

in which

* means the point of linkage to the N atom,

R³ is the side group of a natural α-amino acid or its homologues or isomers, or

R³ is linked to R¹ and the two together form a $(CH_2)_3$ or $(CH_2)_4$ group,

R⁴ is hydrogen or methyl,

R⁵ is $(C_1-C_4)$-alkyl, and

R⁶ is hydrogen or $(C_1-C_4)$-alkyl, or a salt thereof, and (b) a pharmaceutically acceptable excipient.

2. The pharmaceutical composition according to claim 1, wherein

R¹ is hydrogen or $(C_1-C_4)$-alkyl,

R² is hydrogen, and

L is a $(C_2-C_4)$-alkanediyl group or is a group of the formula

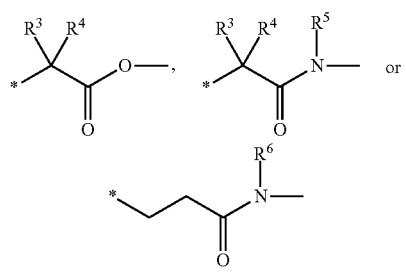

in which

* means the point of linkage to the N atom,

R³ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl, or R³ is linked to R¹ and the two together form a $(CH_2)_3$ or $(CH_2)_4$ group, R⁴ is hydrogen or methyl, R⁵ is methyl, and R⁶ is hydrogen or methyl.

3. The pharmaceutical composition according to claim 1, wherein

R¹ is hydrogen, methyl or n-butyl,

R² is hydrogen, and

L is a $CH_2CH_2$ group or is a group of the formula

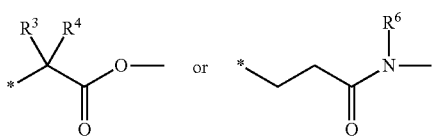

in which

* means the point of linkage to the N atom,

R³ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl, or R³ is linked to R¹ and the two together form a $(CH_2)_3$ or $(CH_2)_4$ group, R⁴ is hydrogen or methyl, and R⁶ is hydrogen or methyl.

4. The pharmaceutical composition according to claim 1, wherein the pharmaceutical composition is suitable for intravenous use.

5. The pharmaceutical composition according to claim 1, further comprising a second active ingredient.

6. The pharmaceutical composition according to claim 5, wherein the second active ingredient is selected from lipid-lowering agents, coronary therapeutics/vasodilators, plasminogen activators and compounds which increase thrombolysis/fibrinolysis, anticoagulants, platelet aggregation-inhibiting substances, fibrinogen receptor antagonists, and antiarrhythmics.

7. A method of treating and/or preventing a thromboembolic disorder comprising administering to a human or animal in need thereof a therapeutically effective amount of a compound of the formula (I)

(I)

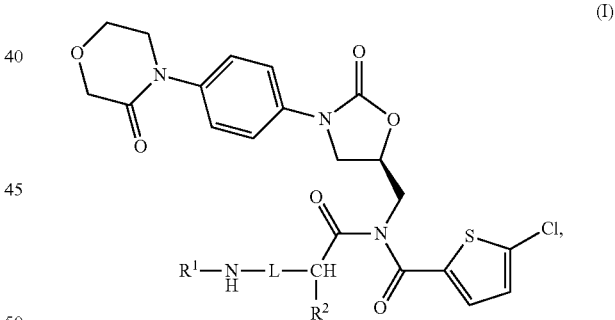

in which

R¹ is hydrogen or $(C_1-C_4)$-alkyl which may be substituted by hydroxy or $(C_1-C_4)$-alkoxy, R² is hydrogen or $(C_1-C_4)$-alkyl, and L is a $(C_1-C_4)$-alkanediyl group in which one $CH_2$ group may be replaced by an O atom, or is a group of the formula

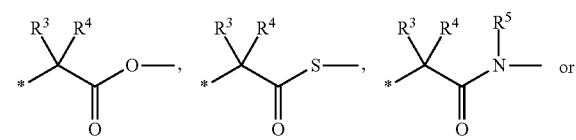

-continued

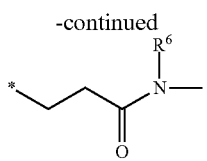

in which
* means the point of linkage to the N atom,
R³ is the side group of a natural α-amino acid or its homologues or isomers,
or
R³ is linked to R¹ and the two together form a (CH₂)₃ or (CH₂)₄ group,
R⁴ is hydrogen or methyl,
R⁵ is (C₁-C₄)-alkyl,
and
R⁶ is hydrogen or (C₁-C₄)-alkyl,
or a salt thereof.

8. The method according to claim 7, wherein
R¹ is hydrogen or (C₁-C₄)-alkyl,
R² is hydrogen,
and
L is a (C₂-C₄)-alkanediyl group or is a group of the formula

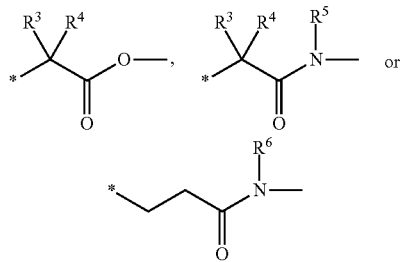

in which
* means the point of linkage to the N atom,
R³ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl,
or
R³ is linked to R¹ and the two together form a (CH₂)₃ or (CH₂)₄ group,
R⁴ is hydrogen or methyl,
R⁵ is methyl,
and
R⁶ is hydrogen or methyl.

9. The method according to claim 7, wherein
R¹ is hydrogen, methyl or n-butyl,
R² is hydrogen,
and
L is a CH₂CH₂ group or is a group of the formula

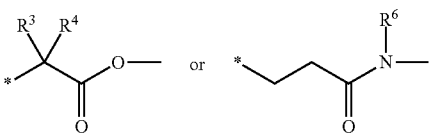

in which
* means the point of linkage to the N atom,
R³ is hydrogen, methyl, propan-2-yl, propan-1-yl, imidazol-4-ylmethyl, hydroxymethyl, 1-hydroxyethyl, carbamoylmethyl, 2-carbamoylethyl, 4-aminobutan-1-yl, 3-aminopropan-1-yl or 3-guanidinopropan-1-yl,
or
R³ is linked to R¹ and the two together form a (CH₂)₃ or (CH₂)₄ group,
R⁴ is hydrogen or methyl,
and
R⁶ is hydrogen or methyl.

10. A method of treating and/or preventing a thromboembolic disorder comprising administering to a human or animal in need thereof a therapeutically effective amount of a pharmaceutical composition according to claim 1.

11. A method of treating and/or preventing a thromboembolic disorder comprising administering to a human or animal in need thereof a therapeutically effective amount of a pharmaceutical composition according to claim 2.

12. A method of treating and/or preventing a thromboembolic disorder comprising administering to a human or animal in need thereof a therapeutically effective amount of a pharmaceutical composition according to claim 3.

13. A method of treating and/or preventing a thromboembolic disorder comprising administering to a human or animal in need thereof a therapeutically effective amount of a pharmaceutical composition according to claim 4.

14. A method of treating and/or preventing a thromboembolic disorder comprising administering to a human or animal in need thereof a therapeutically effective amount of a pharmaceutical composition according to claim 5.

15. A method of treating and/or preventing a thromboembolic disorder comprising administering to a human or animal in need thereof a therapeutically effective amount of a pharmaceutical composition according to claim 6.

* * * * *